United States Patent
Li et al.

(10) Patent No.: US 11,120,894 B2
(45) Date of Patent: Sep. 14, 2021

(54) MEDICAL CONCIERGE

(71) Applicant: ACCENTURE GLOBAL SOLUTIONS LIMITED, Dublin (IE)

(72) Inventors: Chung-Sheng Li, San Jose, CA (US); Guanglei Xiong, Pleasanton, CA (US); Emmanuel Munguia Tapia, San Jose, CA (US); Jingyun Fan, Berkeley, CA (US); Sukryool Kang, Sunnyvale, CA (US); Neeru Narang, San Jose, CA (US); Michael C. Petersen, Austin, TX (US); Dennis P. Delaney, Cedar Park, TX (US)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 191 days.

(21) Appl. No.: 16/163,252

(22) Filed: Oct. 17, 2018

(65) Prior Publication Data
US 2020/0126641 A1 Apr. 23, 2020

(51) Int. Cl.
*G16H 10/00* (2018.01)
*G06Q 40/08* (2012.01)
*G06F 16/22* (2019.01)

(52) U.S. Cl.
CPC ............ *G16H 10/00* (2018.01); *G06F 16/22* (2019.01); *G06Q 40/08* (2013.01)

(58) Field of Classification Search
CPC .............................. G16H 10/00; G06Q 40/08
USPC ........................................................ 705/2–4
See application file for complete search history.

(56) References Cited

U.S. PATENT DOCUMENTS

| | | | |
|---|---|---|---|
| 6,955,646 B2 * | 10/2005 | Christ ................. | A61B 5/0002 600/300 |
| 7,725,335 B1 * | 5/2010 | Goodwin ............. | G06Q 40/08 705/4 |
| 7,917,378 B2 | 3/2011 | Fitzgerald et al. | |
| 8,554,582 B2 * | 10/2013 | Ikeda .................. | G06F 16/245 705/4 |
| 2014/0006065 A1 * | 1/2014 | Olaniyan ............. | G06F 19/328 705/4 |
| 2017/0235885 A1 * | 8/2017 | Cox .................... | G06F 40/284 705/2 |

OTHER PUBLICATIONS

Gottlieb, Joshua D., Adam Hale Shapiro, and Abe Dunn. "The complexity of billing and paying for physician care." Health Affairs 37.4 (2018): 619-626. (Year: 2018).*

* cited by examiner

*Primary Examiner* — Mark Holcomb
(74) *Attorney, Agent, or Firm* — Mannava & Kang, P.C.

(57) ABSTRACT

Examples of medical concierge are provided. In an example, an claim may be received. The claim may include data relating to service provided, by a provider, to multiple patients. The claim may be parsed to determine the provider, the multiple patients and the service provided. Additional information may then be fetched. The additional information may include one of a number of claims filed in the past, status of each claim, number of appeals filed, status of the appeals, and complaints registered by the provider. Thereafter, the claim and the additional information may be analyzed and a category may be determined for the provider. The category may be determined based on a behaviour model that may be computed based on the claim and the additional information. The category may be indicative of an issue in behaviour of the provider.

14 Claims, 16 Drawing Sheets

Cybersyn, LLC
Exhibit 1010
Page 1 of 1

MEDICAL CONCIERGE

BACKGROUND

In the modern health and medical industry, service providers such as doctors and physicians, have cures and treatments for a large number of diseases and illnesses. With the involvement of latest techniques and advances in technology, the diagnoses have become precise and the treatments have become more effective thereby enhancing patient satisfaction and average lifespan. The ease and convenience of accessing medical services has also grown manifold. Patients can contact doctors over phone or chat to have medicines and treatment for an ailment and pay doctors online or through their mobile devices.

Various medical companies offer medical plans to patients, for covering patients against medical expenses and providing flexibility in payments. The patients register with such companies for a medical plan to avail the benefits. When a patient is treated by a service provider, referred to as a provider, then fees and expenses incurred by the patient is raised through a claim submitted by the provider to a company, also referred to as a payer, with which the patient may be registered. In an example embodiment, the claim submitted may be an insurance claim. The provider may submit claims for multiple patients to the payer and the payer upon receiving the claims may verify the claims submitted by providers and make the payments upon successful verification. Payers may also have automated systems for receiving the claims, verifying authenticity of the claims and process the payments for the providers.

However, the existing systems are resource and time intensive and consume substantial amount of time to complete the process of verifying claims and processing the payments. Such systems are inefficient and are often unable to proceed due to incomplete or incorrect verification, incomplete information or unavailability of data related to the providers, thereby having reduced user satisfaction. The systems are passive and do not take proactive measures to detect and resolve an issue in the process. Further, current systems are unable to collect and analyze data related to the providers on a real time basis so as to proactively support the payers and the providers.

The present disclosure provides a technical solution to a problem to efficiently and proactively provide service to the employees of an enterprise.

BRIEF DESCRIPTION OF DRAWINGS

Features of the present disclosure are illustrated by way of examples shown in the following figures. In the following figures, like numerals indicate like elements, in which.

DETAILED DESCRIPTION

Figure 1:
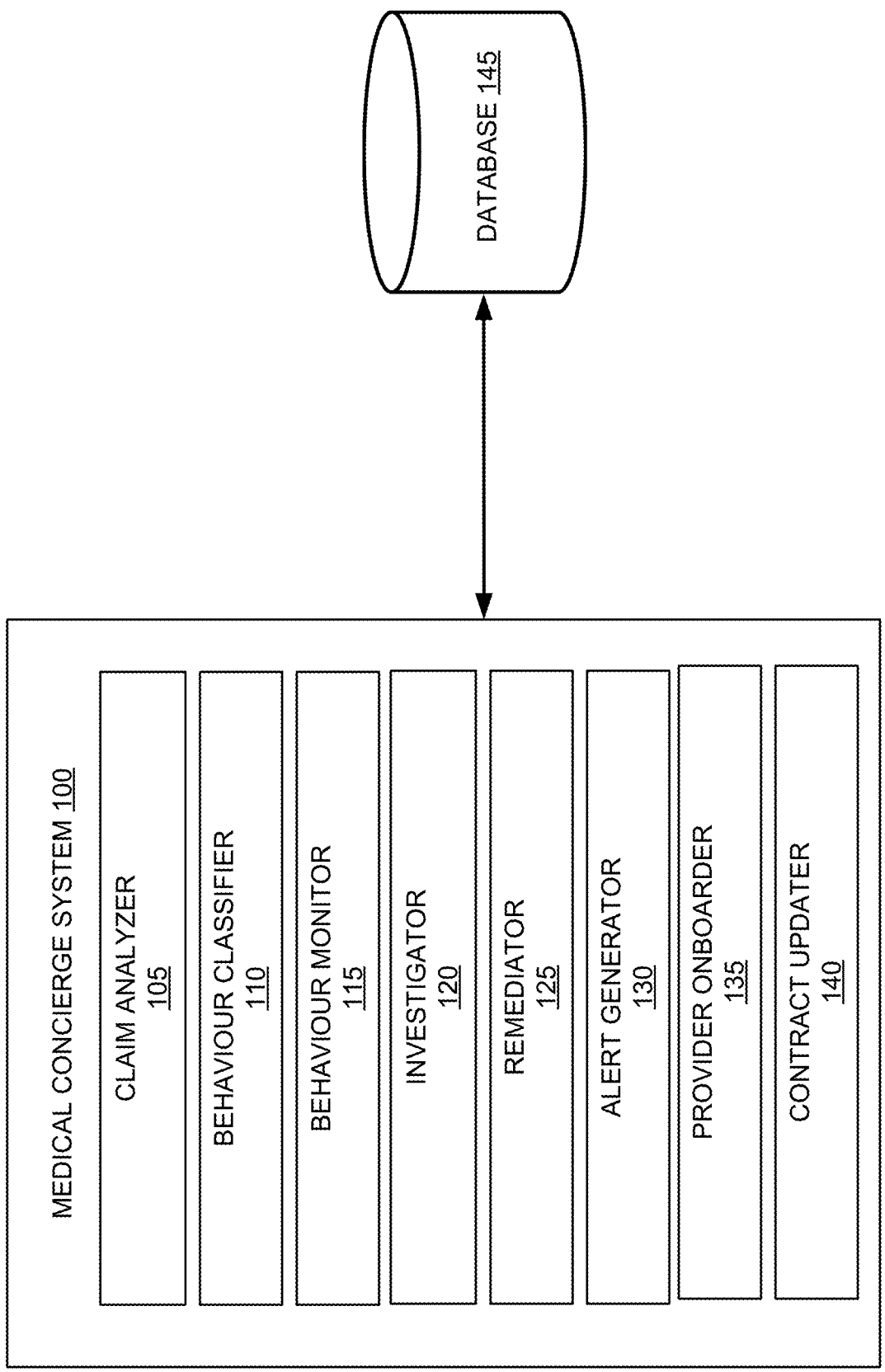
FIG. 1 illustrates various components of a medical concierge system, according to an example embodiment of the present disclosure.

For simplicity and illustrative purposes, the present disclosure is described by referring mainly to examples thereof. The examples of the present disclosure described herein may be used together in different combinations. In the following description, details are set forth in order to provide an understanding of the present disclosure. It will be readily apparent however, that the present disclosure may be practiced without limitation to all these details. Also, throughout the present disclosure, the terms "a" and "an" are intended to denote at least one of a particular element and can include one or more of such elements. As used herein, the term "includes" means includes but not limited to, the term "including" means including but not limited to. The term "based on" means based at least in part on, the term "based upon" means based at least in part upon, and the term "such as" means such as but not limited to.

The present disclosure describes systems and methods for providing medical concierge services to providers and payers for filing and processing claims in an efficient and proactive manner. The services may be provided by an automated system that stores data related to the providers, claims filed by the providers, number of patients visiting the providers, and supports and resolves issues in filing and processing of the claims based on behaviour modeling of the providers.

Providers, such as doctors, physicians, and other medical practitioners providing services to patients, may have issues in filing claims. For instance, for filing a claim, a provider may provide incomplete data or may forget to fill a particular column or row of data in an online form. The claim may therefore be rejected or denied every time the provider files the claim through the online form. Under certain cases, the provider may also file the claim with data and information that is different or exceeds limits specified in a medical policy of the claim. This may occur, for instance, when a patient required more number of visits to the provider due to a severe medical condition and therefore the actual number of visits exceeded a limit of visits specified in the medical policy. In another example, the provider may have a habit of providing false information about the number of visits, treatment plans, and the medical expenses for the patients during filing of the claim.

Apart from filing related issues that lead to unwanted denials or rejections of claims, the providers may also experience process related issues. For instance, providers may have to wait for long for their payments to process and are generally not aware of a reason for the delay in the process.

The present disclosure provides for efficient and proactive analysis of an issue in behaviour of the provider in filing the claims, and an appropriate remedy for addressing the issue thereby expediting the overall process. Further, the present disclosure provides for identification of providers submitting false data to eliminate and minimize such practices.

According to an aspect of the present disclosure, a claim may be received from a provider. The claim may include data relating to service provided by the provider to multiple patients. The data may include number of visits by the multiple patients, treatments suggested by the provider, and medical expense for each patient. In an example, the claim may be submitted to a payer with which the multiple patients may be registered. The claim may then be parsed to determine the data included in the claim. For instance, to identify details of the provider, and the multiple patients. The claim may also be parsed to determine the details of the service provided by the provider to the multiple patients.

After determining the provider, additional information related to the provider may be fetched. The additional information may include information related to number of claims filed in the past, status of each claim for approval, denial and rejection, number of appeals filed by the provider, status of the appeals as approved and denied, and complains registered by the provider. In one example, the additional information may be fetched from various sources such as online and public databases, internal databases, staff members of the provider, and patients visiting and treated by the provider. Thereafter, the claim and the additional information may be analyzed. In the analysis, the number of claims denied, the number of claims rejected, the number of claims approved, the number of appeals filed, the number of appeals approved, and the number of appeals denied may be computed and compared with a predefined threshold. The predefined threshold may be determined based on analysis of history of inquiries or appeals filed after claims have been rejected, denied or adjusted. The threshold value may be calculated based on a simple model, such as an average of number of claims rejected, denied or adjusted or based on a sophisticated model, for instance, a machine learning model.

In an example, if the predefined threshold is exceeded, then a type of behaviour of the provider may be determined. The type of behaviour may be indicative of an issue in filing the claim and may be classified into three categories, such as a necessity for a patient, a compliant provider, and a malicious provider. The category necessity for a patient may include behaviour of providing information that is deviant from a prescribed limit or data specified in the medical policy of the claim, where the deviation may have occurred due to medical necessity for the patient. For instance, if a patient needed to have more medicines and a rigorous treatment plan, then the expense may exceed a limit specified in the medical policy.

For the category, compliant provider, the provider may commit an error or mistake due to unawareness of process of filing the claim. This may include missing some information during filing of the claim or selecting an incorrect category or an option in a form. Further, the category malicious provider may include behaviour whereby the provider may regularly provide false information and data to claim amount higher than what was actually incurred.

Once the provider is categorized into one of the categories, the provider is monitored for changes in the behaviour. In one example, monitoring may include determining a change in rate of one of claim denials and claim adjustments. If there is a change in one of the claim denials and the claim adjustments, then an investigation may be initiated. The investigation may be performed to determine causes of the behaviour shown by the provider. During the investigation, multiple hypotheses may be generated and evidences may be collected for the multiple hypotheses. Based on the evidence collected, a hypothesis may be selected from amongst the multiple hypotheses. After determining the hypothesis, a remedy may be determined and provided to the provider for addressing the issue.

For example, if the provider is providing an incomplete data for filing the claim, then a cause, unawareness of process of filing the claim may be deduced. Thereafter, multiple hypotheses, such as the provider not properly trained to file the claim, the software for filing the claim being outdated, and a staff member being untrained for providing a code may be determined. Thereafter, evidence such as data records related to training of the provider, version of the software and skill and expertise of the staff member may be retrieved from internal databases. Based on evidence collection, the hypothesis of the staff member being untrained may be determined and the remedy of scheduling a training for the staff member may be proposed. The hypothesis may then be notified through an alert to the provider along with the remedy for implementation.

Thus, systems such as, for example, medical concierge systems, which use techniques consistent with the present disclosure may proactively detect issues in behaviour of providers in filing the claim and provide a remedy to the provider for efficient rectification. The medical concierge system provides resource and time efficient techniques for resolving issues and expedites processing of the claims.

FIG. 1 illustrates a medical concierge system 100 for providing support services to payers, and providers, according to an example embodiment of the present disclosure. In an example embodiment, the medical concierge system 100, hereinafter referred to as system 100, uses a combination of Artificial Intelligence (AI) techniques, such as machine learning, data mining, and knowledge discovery, for the purpose, of providing services to the payers and the providers.

In an example, the system 100, amongst other components, may include a claim analyzer 105, a behaviour classifier 110, a behaviour monitor 115, and an investigator 120. The system 100 may also include a remediator 125, an alert generator 130, a provider onboarder 135, and a contract updater 140. The system 100 may be communicatively coupled to a central database 145.

The system 100 provides for a proactive and efficient support services to the payers and providers. In an example, the support services may be provided for behaviour modeling of provider, issue detection, providing remedies, and provider onboarding. Behaviour modeling may be performed to categorize behaviour of a provider for filing claims and determining issues in the behaviour during filing of the claims. Upon detection of an issue in the behaviour, an investigation is performed and a remedy is determined to mitigate the issue.

In an example, the system 100 may monitor the behaviour based on number of claims filed by the provider, status of the claims filed and number of appeals filed by the provider. The system 100 may also monitor for change in behaviour of the provider and based on the change in behaviour, the system 100 may categorize the provider into a new category. The new category for providers may include, for instance, a normal category, an occasional mistakes category, a frequent mistakes category, an occasional inquiry and frequent inquiry category. The provider may be categorized based on the behaviour modeling of historical data or claims that may have been rejected due to coding errors, the statistical pattern of inquiries, and appeals filed regarding previous claims. The behaviour model may be one of a finite state machine, a hidden markov model, and a simultaneous first order differential equation. Each of these models has parameters and the parameters may be calculated from the historical data. An algorithm utilized for classifying the categories of the provider may be based on a simple regression technique or a sophisticated machine learning model, such as Support Vector Machine (SVM). Based on the category of the provider, an investigation may be conducted to provide a remedy.

In an example embodiment of the present disclosure, the claim analyzer 105 may receive an claim filed by a provider. The claim may include information related to the provider, multiple patients treated by the provider and the details of the service provided. The details of the service may include number of visits by the patients to the provider, type of diagnosis, and treatment plans. The claim analyzer 105 may determine the information from the claim. Thereafter, the claim analyzer 105 may fetch additional information related to the provider and the claim. The additional information may include number of claims filed by the provider, status of each claim whether approved or denied, number of appeals filed and the status of each appeal.

The behaviour classifier 110 may then generate a behaviour model for the provider. In one example, the behaviour model may be generated based on a formulation of type of behaviour model, such as one of a finite state machine, a hidden Markov model, or any other model. The behaviour model may be indicative of a behaviour pattern of the provider for filing the claims. For instance, whether the provider is repeatedly committing any error in filing the claims, whether the provider is providing false information with inflated data about the number of visits by the patients, service charges of the provider and other medical expense of the provider, or whether there was a medical necessity for a patient to treat the patient more frequently than a treatment plan as per limits specified in a medical policy of the claims. Accordingly, the behaviour of the provider may be classified into three categories, a compliant provider, a malicious provider and a necessity for a patient. In one example, the behaviour classifier 110 may generate the behaviour model based on the claims and the additional information. After generating the behaviour model, the behaviour classifier 110 may categorize the provider in any one of the three categories.

In one example, the behaviour monitor 115 may continuously monitor the behaviour of the provider for various parameters that indicate if there has been a change in behaviour of the provider. For instance, if there has been change in the number of claims filed by the provider, number of appeals filed, number of visiting patients, reviews and ratings of the provider. The change in number of claims filed may be for instance, if there has been a rise in number of claims filed by the provider in last four months or there has been a sharp fall in filing of claims by the provider. In a case, where number of patients increase then the number of filed claims filed may also increase. Other parameters such as fall in number of appeals filed and poor ratings and feedback of the provider may also indicate that the behaviour of the provider is changing. The behaviour monitor 115 may also determine if three is a change in claim denials or adjustments for the provider. The behaviour monitor 115 may then determine a change in behaviour of the provider. Based on the change detected by the behaviour monitor 115, the behaviour classifier 110 may determine if the provider may still be in the previous category or may have to be switched to another category. The behaviour classifier 110 may accordingly, update the category of the provider.

The objective of identifying the category of the provider is to determine a behaviour type for the provider and perform an investigation and remediation accordingly, as each category may require a particular type of investigation and remediation. In an example, based on the category of the provider, the investigator 120 may investigate to determine an issue with the behaviour of the provider. For instance, if the provider is compliant and is repeatedly making mistake in filling one or two columns of data during filing of the claim then the issue may be lack of awareness of those particular data. In another example, if the provider is every time providing false data relating to number of visiting patients or treatment plan suggested to claim a higher amount then the issue may be misrepresentation of data.

After determining the issue, the investigator 120 may generate multiple hypotheses and collect evidence related to the multiple hypotheses. The investigator 120 may then select a hypothesis based on relevance of the evidence to the hypotheses. For example, if the provider falls in the category necessity for a patient, then the data and information provided may be different from limits specified in a medical policy of the claim. The investigator 120 may determine necessity for patient A, necessity for patient B and necessity for patient C as multiple hypotheses. For each hypothesis, the investigator 120 may retrieve evidence for data related to medical conditions of patient A, patient B and patient C, medical history of the patients A, B, and C, and effect of treatment on the patients A, B, and C. After collecting the evidence, the investigator 120 may determine medical conditions of the patient B to be relevant based on matching with the data provided in the claim. Thereafter, the investigator 120 may select the hypothesis necessity for patient B from the multiple hypotheses for remediation.

The remediator 125 may analyze the hypothesis and collect data relating to reviews and complaints from social media. For analyzing the hypothesis, the remediator 125 may formulate a hypothesis based on, for instance, frequent coding mistakes in filing claims by an inexperienced staff, aggressive claim filing, or inconsistent filing between the diagnosis and procedure performed. Further, the remediator 125 may collect evidences for formulating hypotheses, wherein different evidence may be collected for each hypothesis. The remediator 125 may also collect additional evidence from social media, such as the reviews and complaints of the provider and physician. The remediator 125 may then determine a remedy to resolve the issue related to the provider behaviour. The remedy may be for instance, whether the provider requires training for filing the claims, whether the staff of the provider requires training, whether the software requires an upgrade. Further, the alert generator 130 may generate an alert and notify the issue along with the remedy to the provider.

The provider onboarder 135 may determine a change in a provider profile based on one of information shared by the provider and detecting a change in practice of the provider. The practice includes one of a solo practice and a group practice. In an example, the change in practice may include a change of services provided and a change of physicians included in the practice. The change in practice may be detected through information directly shared by the provider, such as through provider update or indirectly from information retrieved from other sources including publicly available information. The provider onboarder 135 may then fetch information relating to a new profile and accordingly may update the profile of the provider with the information. The provider onboarder 135 may then store the updated profile of the provider in the database 145.

The provider and a payer generally have a contract between them to determine policies, and rules applicable to regulate various transactions between the provider and the payer. The contracts include multiple definitions and policies that are utilized for regulating relationship between the two. In an example, upon detection a change in profile of the provider, the various definitions being affected by the update may also have to be updated. For instance, if there is a clause related to liability in a group practice in the contract and the practice of the provider has changed to solo practice, then the clause of liability may have to be updated to include liability as per the solo practice.

The contract updater 140 may parse an existing contract with the provider to determine multiple definitions. The contract updater 140 may then determine if a definition from amongst the multiple definitions may have to be updated based on the change in the profile of the provider. This may be determined by comparing if the updated profile of the provider is covered under the definitions in the existing contract. If not, then the definitions may have to be updated. Thereafter, the contract updater 140 may change the definition and update the existing contract. The working of the system 100 with respect to additional components is explained in details with the help of examples with reference to description of subsequent figures.

Figure 2:
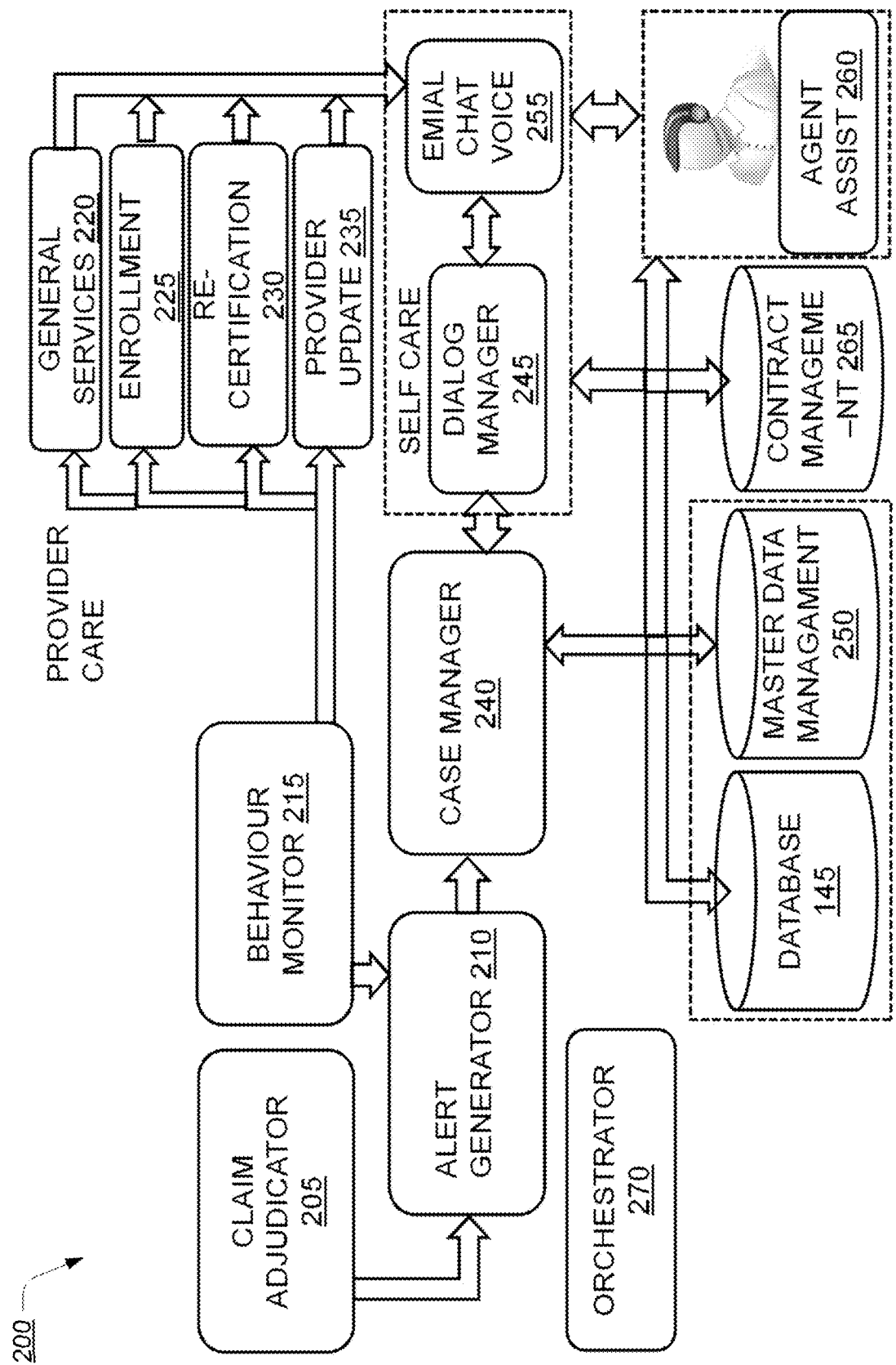
FIG. 2 illustrates an example depicting working of the components of the medical concierge system, according to an example embodiment of the present disclosure.

FIG. 2 illustrates a block diagram 200 for working of the system 100 with additional components, according to an example embodiment of the present disclosure. The claim adjudicator 205 may receive the claims filed by the provider. The claim adjudicator 205 may then determine whether the claims filed by the provider are approved, denied, rejected or adjusted. If the claim is approved then the alert generator 210 may generate the alert for the approval. The behaviour monitor 215 may also monitor the behaviour of the provider to detect a change. The behaviour monitor 215 may monitor the general services 220 provided by the provider, enrollment 225 of the provider, re-certification 230 required for the provider, and provider update 235 for the provider. The general services 220 may include, for example, internal medicines, dental, and Obstetrician Gynecologist (OBGYN). The enrollment 225 may include onboarding a new practice or a new provider, verifying licenses of the new provider and the history of malpractice lawsuits against or filed by the new provider. After the provider is onboarded, the provider may be recertified after a period of time. As part of the recertification process, the practice may have to update current status of the practice. This may include, for example, the on-boarding of new providers in the practice and the exiting of previous providers from the practice.

Upon detecting a change, the alert generator 210 may generate an alert for the provider. A case corresponding to the provider may be established by the case manager 240. The case manager 240 may determine the next step to be taken for the case. For instance, depending upon a condition, the case manager 240 may determine if the case is to be forwarded to a dialog manager 245 or to be stored in the master data management 250 and the database 145. If the case is stored in the master data management 250, then the case may be utilized later for deriving hypotheses for investigation of the case for the provider. In one example, the dialog manager 245 may allow the provider to discuss the issue through an email, chat and voice module 255. In case the provider may need more assistance, the provider may be directed to a human agent assist 260. In an example, the dialog manager 245 may also provide the case to a contract management 265 for storing. The orchestrator 270 may coordinate the flow of the case between the components.

Figure 3:
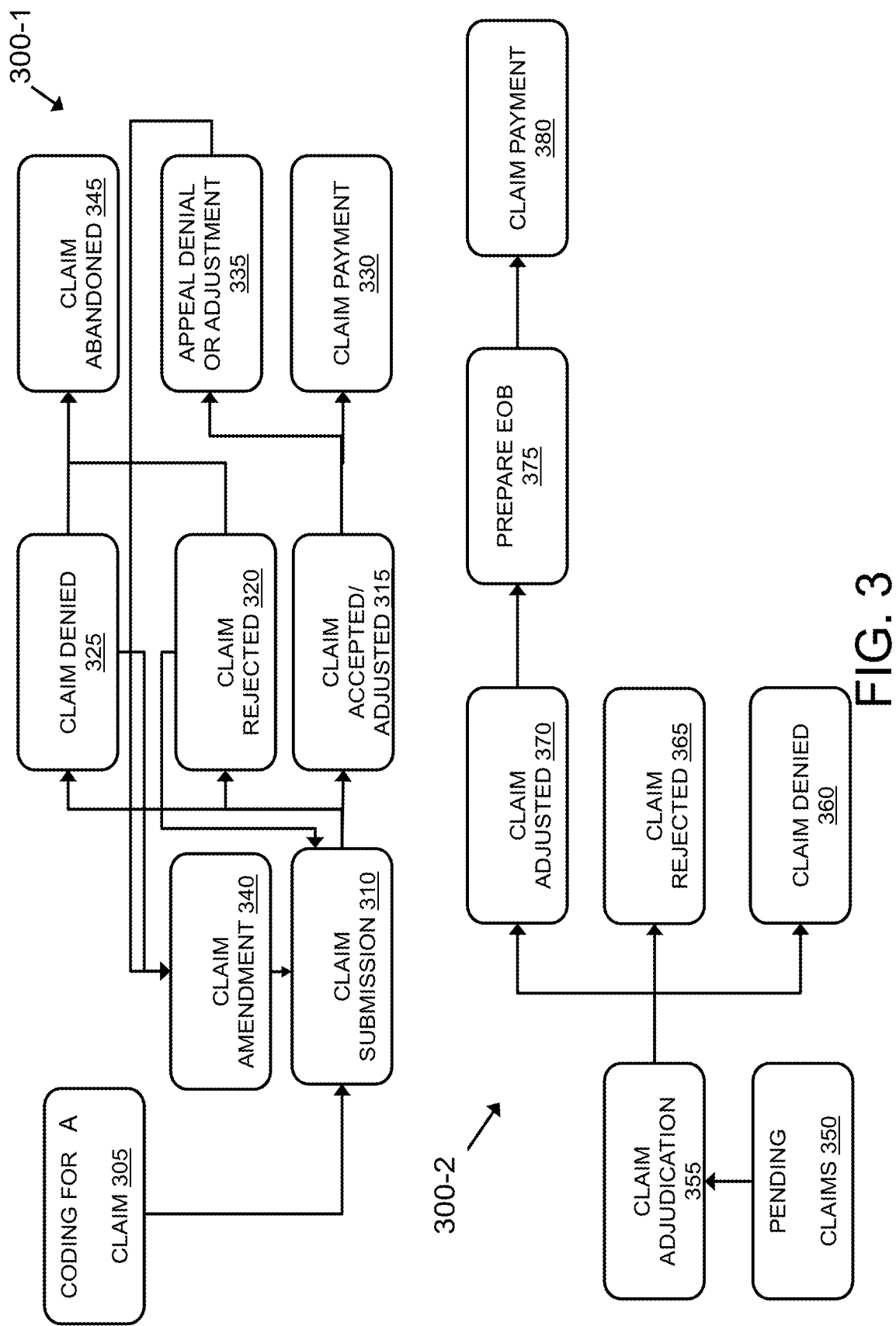
FIG. 3 illustrates an example depicting processing of claims for a provider, according to an example embodiment of the present disclosure.

FIG. 3 illustrates a block diagram for processing claims, wherein 300-1 shows an claim being submitted by the provider and processed and 300-2 shows the claims being processed by the payer. Referring to block 305, a coding for the claim may be submitted. There may be multiple codes for each claim and during submission of the claims, the provider may select an appropriate code to be submitted. The claim may be submitted at 310. After submission of the claim, the claim may be accepted or adjusted at 315. The adjustment may include approving a lesser amount than the amount claimed by the provider. This may be because of the amount computed based on assessment of the claim by the payer. The claim may also be accepted, wherein the complete amount as claimed in the claim may be provided to the provider. In one example, the claim may be rejected at block 320. The claim may be rejected because of any error during filing of the claim or selecting an appropriate code for submission. After rejection of the claim, the provider may have a chance of refiling the claim. The claim may also be denied at 325, wherein the amount may have been disapproved by the payer. In such a case, the provider may amend the claim and submit the claim again at block 310.

In an example, when the claim has been accepted or adjusted, then the payment for the claim may be performed at block 330. An appeal for the claim may also be filed that may be denied or adjusted at block 335. In case the appeal is denied or adjusted, the claim may be amended at block 340 and then submitted at 310. In an example, when the is denied or rejected, then the claim may be abandoned at block 345.

Referring to 300-2, at block 350 pending claims may be submitted for adjudication. At block 355, each of the pending claims may be adjudicated. Each claim may either be denied at 360, rejected at block 365 or adjusted at block 370. If the claim is adjusted then an Explanation of Benefit (EOB) may be prepared by the payer at block 375. After preparing the EOB, a payment corresponding to the claim may be performed at block 380.

Figure 4:
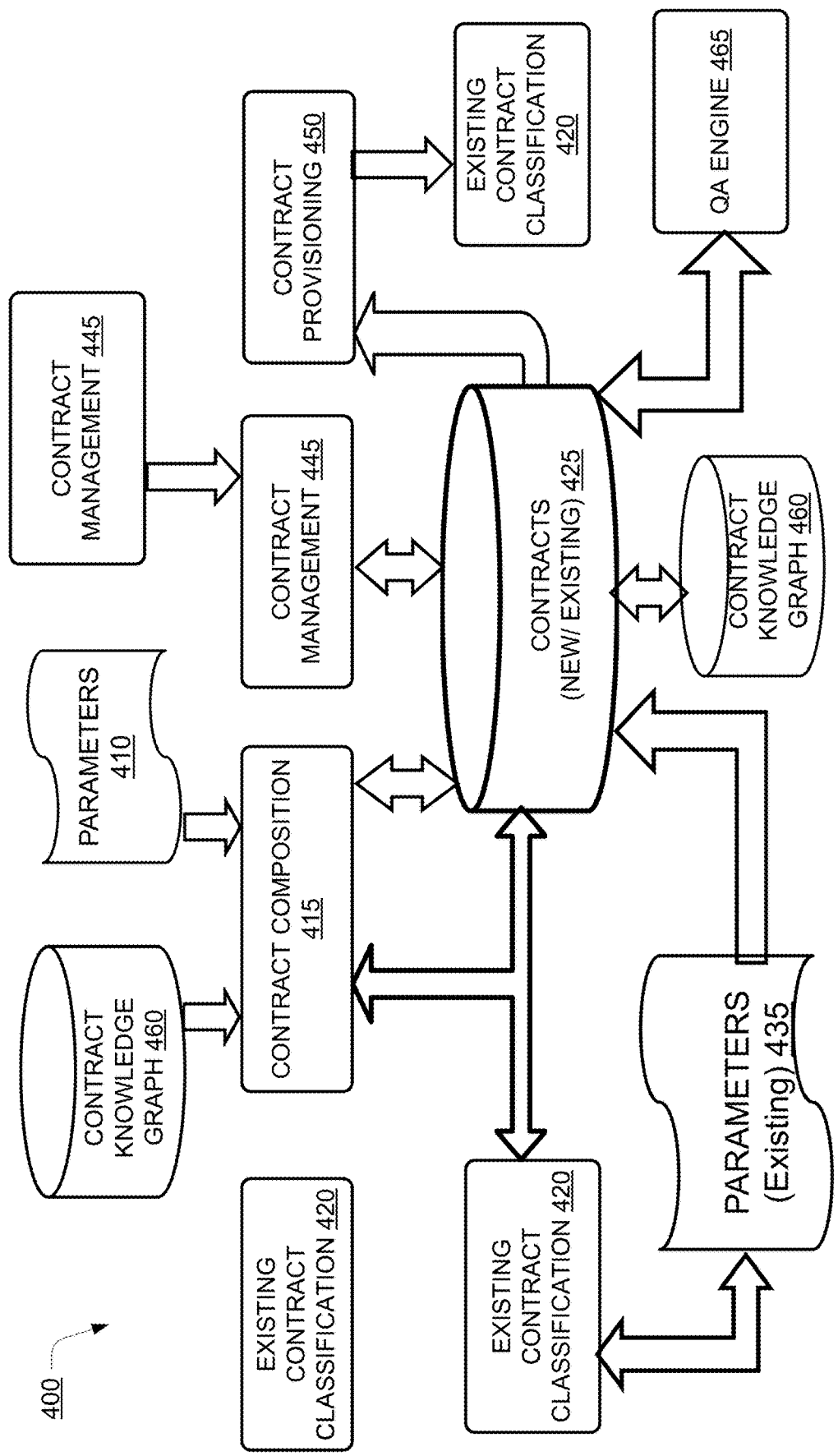
FIG. 4 illustrates an example depicting making a contract and updating the contract, according to an example embodiment of the present disclosure.

FIG. 4 illustrates a block diagram 400 for making a contract and updating the contract, according to an example embodiment of the present disclosure. Contract templates 405 and parameters 410 may be provided for contract composition at 415. The contract templates 405 provide an overall structure to the contract and allow quick and efficient composition of contracts. The parameters 410 may include various definitions to be included in the contract. In one example, the contract composition 415 may utilize existing contract classification 420 to compose contracts. In one example, the existing contract classification 420 may include different types of contracts for providers belonging to different categories. For instance, a particular type of contracts for providers belonging to the category compliant provider. In another example, the existing contract classification 420 may include contracts belonging to specialized providers, such as different contracts for physician, heart surgeon and physiotherapist.

The contracts may then be stored in a contracts 425 database. The contracts 425 may also store information received from information extraction 430 and parameters 435 for existing contracts. In one example, the information extraction 430 may extract information from a contract including the scope of the provider services and pricing plan for each service provided. The pricing plan may be based on criteria defined by an organization, such as Medicare or Medicaid. For instance, the pricing plan may include a price of around 150% or at a rate specified by the organization. In case of updating a contract at block 440, information related to the updated contract may be provided to the contract management 445. The contract management 445, in one example, may incorporate additional information in the contracts to update the contracts. Based on information received from the contracts management 445 new contracts may be generated or an existing contract may be updated. The contracts 425 database may provide information related to the contracts for contract provisioning at 450. The contract provisioning 450 may provision and codify the contracts between the payer and the provider. The claim adjudicator 455 may adjudicate the claims based on the contracts between the payer and the provider. In one example, the contracts 425 may receive information from contract knowledge graph 460 about various policies and clauses to be included in contracts. A Question Answer (QA) engine 465 may also be coupled to the contracts 425 for querying the contracts 425 for information and retrieve the information from the contracts 425.

Figure 5:
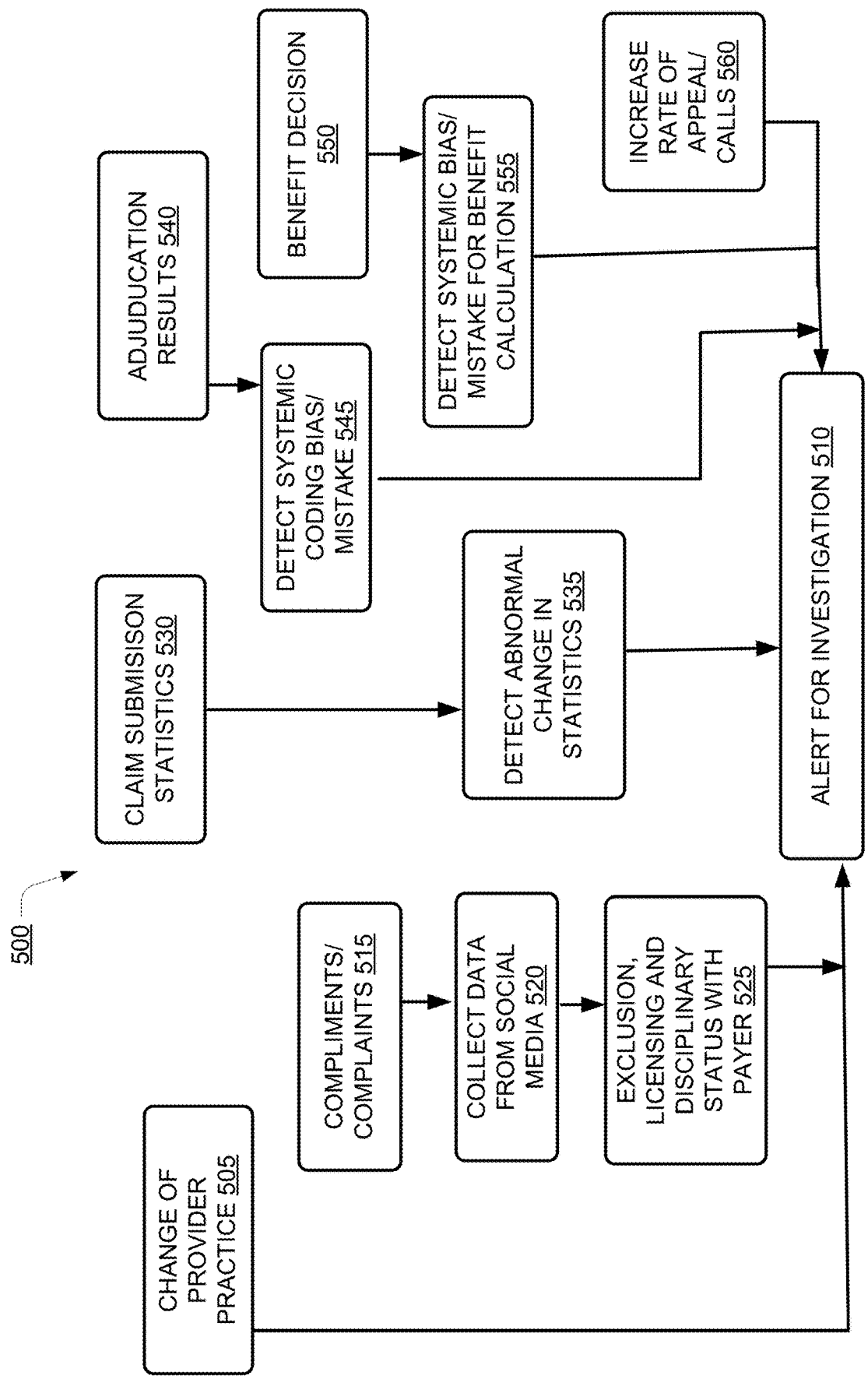
FIG. 5 illustrates a block diagram for generating an alert for investigation, according to an example embodiment of the present disclosure.

FIG. 5 illustrates a block diagram 500 for generating an alert for investigation, according to an example embodiment of the present disclosure. The diagram 500 illustrates various conditions under which the alert for investigation may be generated and an automated investigation may be performed. For instance, if there is a change in provider practice at block 505, from a solo practice to a group practice then the alert for investigation at block 510 may be initiated. In an example, compliments or complaints may be analyzed for a provider at block 515. Thereafter, data from social media may be collected regarding the compliments and complaints regarding the compliments or complaints at 520. The exclusion, licensing and disciplinary status with the payer may also be checked at block 525 and accordingly the alert may be generated. In an example, the exclusion may refer to providers that are excluded from some plans enrolled by the payers, due to higher fees charged by the providers for providing service and care. The exclusion of the providers may aid the payers in managing overall cost of the healthcare plan. At block 530, claim submission statistics may be analyzed. The claim submission statistics may include past claim submissions by a provider, number of claims accepted or rejected, number of claims submitted by other providers along with status of the submitted claims for other providers.

Thereafter, abnormal changes in the statistics of the claim submissions may be determined at 535. If the change is detected then an alert for investigation is triggered. In another example, adjudication results may be received and analyzed at block 540. At block 545, a mistake related to coding bias may be detected. For instance, an incorrect code entered for filing of the claim may be detected. In case, the mistake for entering the code is detected then the alert may be generated. In an example, at block 550, a benefit decision may be received, and then a mistake or systemic bias for benefit calculation may be detected at 555. For instance, as per calculation by the payer if the payment to be made to the provider is less than what is filed by the provider in the claim, then the alert may be generated. In another example, if the rate of appeals or calls increases at block 560, then the alert may be generated.

Figure 6:
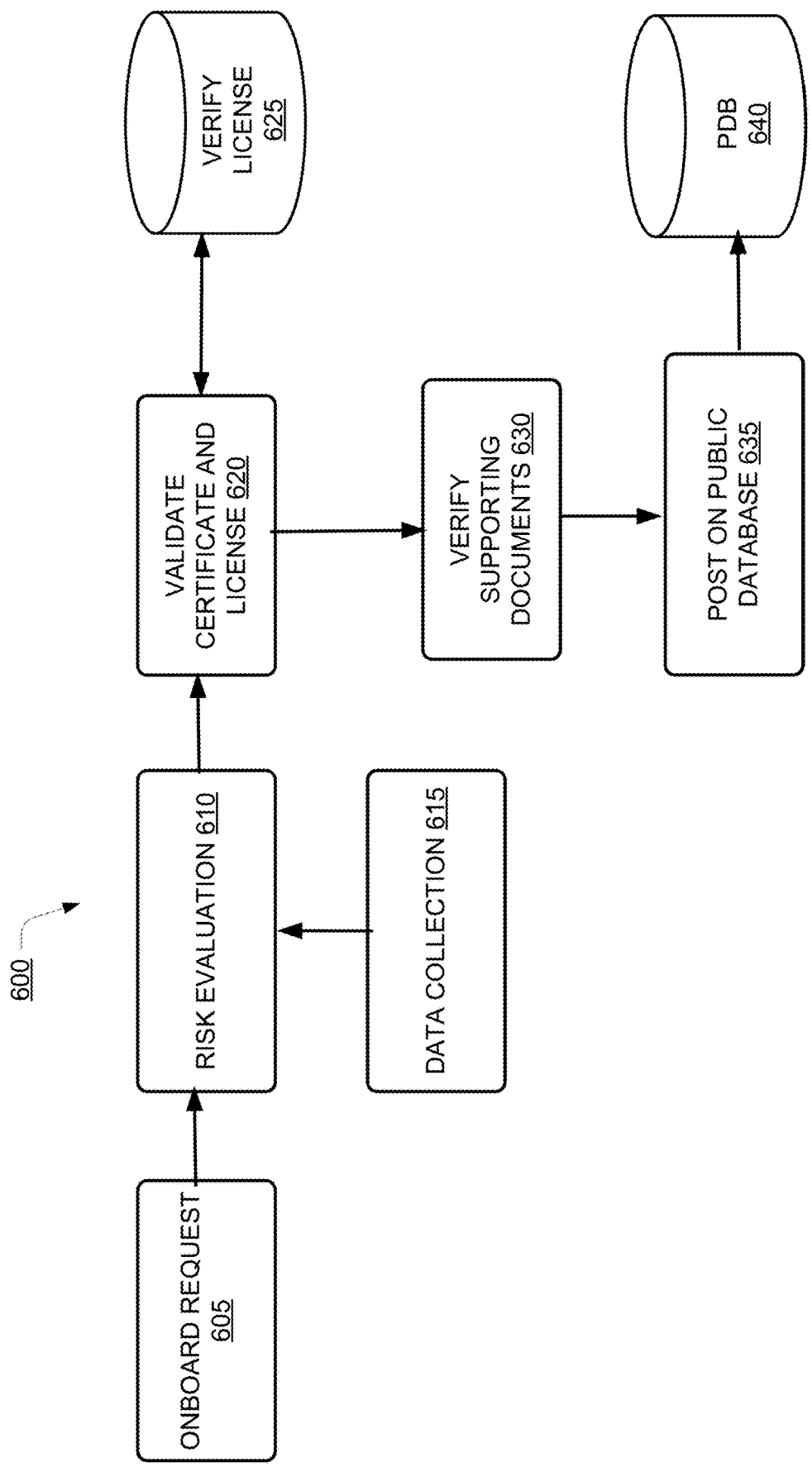
FIG. 6 illustrates an example depicting onboarding of providers, according to an example embodiment of the present disclosure.

FIG. 6 illustrates a block diagram 600 for onboarding providers with the system 100 for processing of the claims, according to an example embodiment of the present disclosure. At block 605, an onboard request may be received. The onboard request may be received from the provider for registering and onboarding. After receiving the onboard request, a risk related to the onboarding may be evaluated at 610. The evaluation may include determining and assessing history of the provider and past performance of the provider in treating patients and filing claims. For risk evaluation, data collection may be performed at block 615. In one example, the data may be collected from various sources, such as databases, previous group members and facility owners.

In one example, after evaluation of the data certificates and licenses of the provider may be validated at block 620. For validation, the licenses may be verified from a database storing the licenses of the provider at 625. After verifying the licenses, the supporting documents related to certificates and licenses, such as experience certificates, engagement letters, qualification certificates may also be verified at 630. Thereafter, the information regarding the provider may be posted on public database at 635 and stored in public database 640. Further, various conditions under which the onboarding of the provider may be initiated is explained in details with the help of examples with reference to description of FIG. 7.

Figure 7:
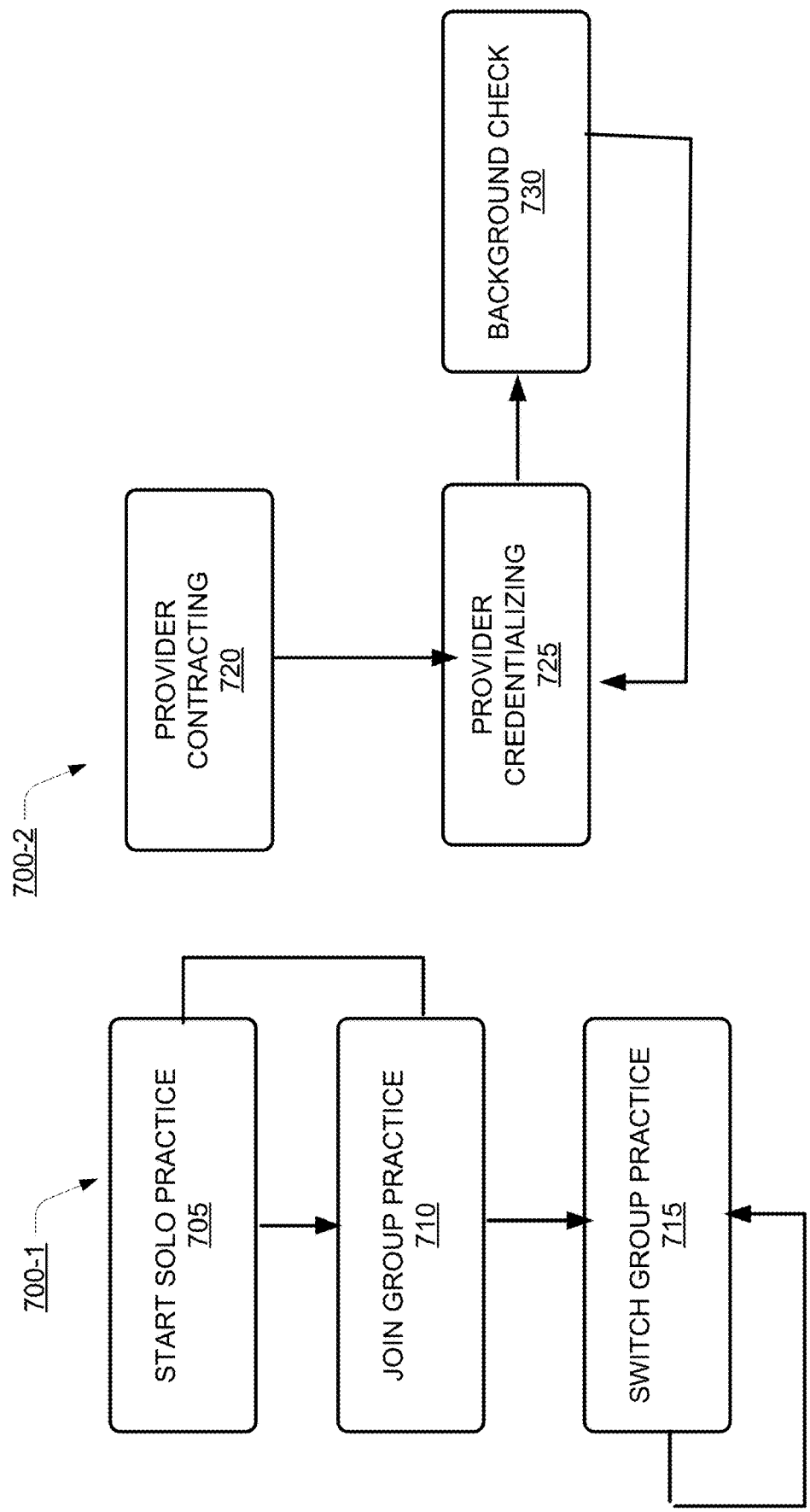
FIG. 7 illustrates an example depicting various events for onboarding of providers, according to an example embodiment of the present disclosure.

FIG. 7 illustrates a block diagram 700 for determining various events when the onboarding is performed according to an example embodiment of the present disclosure. The block diagram 700-1 shows change in practice of a provider for onboarding and 700-2 shows process performed during onboarding of the provider. Referring to block 705, when the provider may start a solo practice then the onboarding may be performed. At block 710, when the provider may join a group practice then the onboarding of the provider may be required. In an example, when the provider switches from one practice to another, at block 715, for instance, from solo practice to the group practice or from group practice to the solo practice, the onboarding may be performed. At block 720, when the provider may be onboarded, then an existing contract may be updated or a new contract may be established for the provider. Thereafter, at block 725, provider credentials, for instance, certificates, degrees, and other documents indicative of qualification and expertise of the provider may be verified. In one example, verifying the provider credentials may require performing background check on the provider regarding the qualification, certificates and licenses of the provider.

Figure 8:
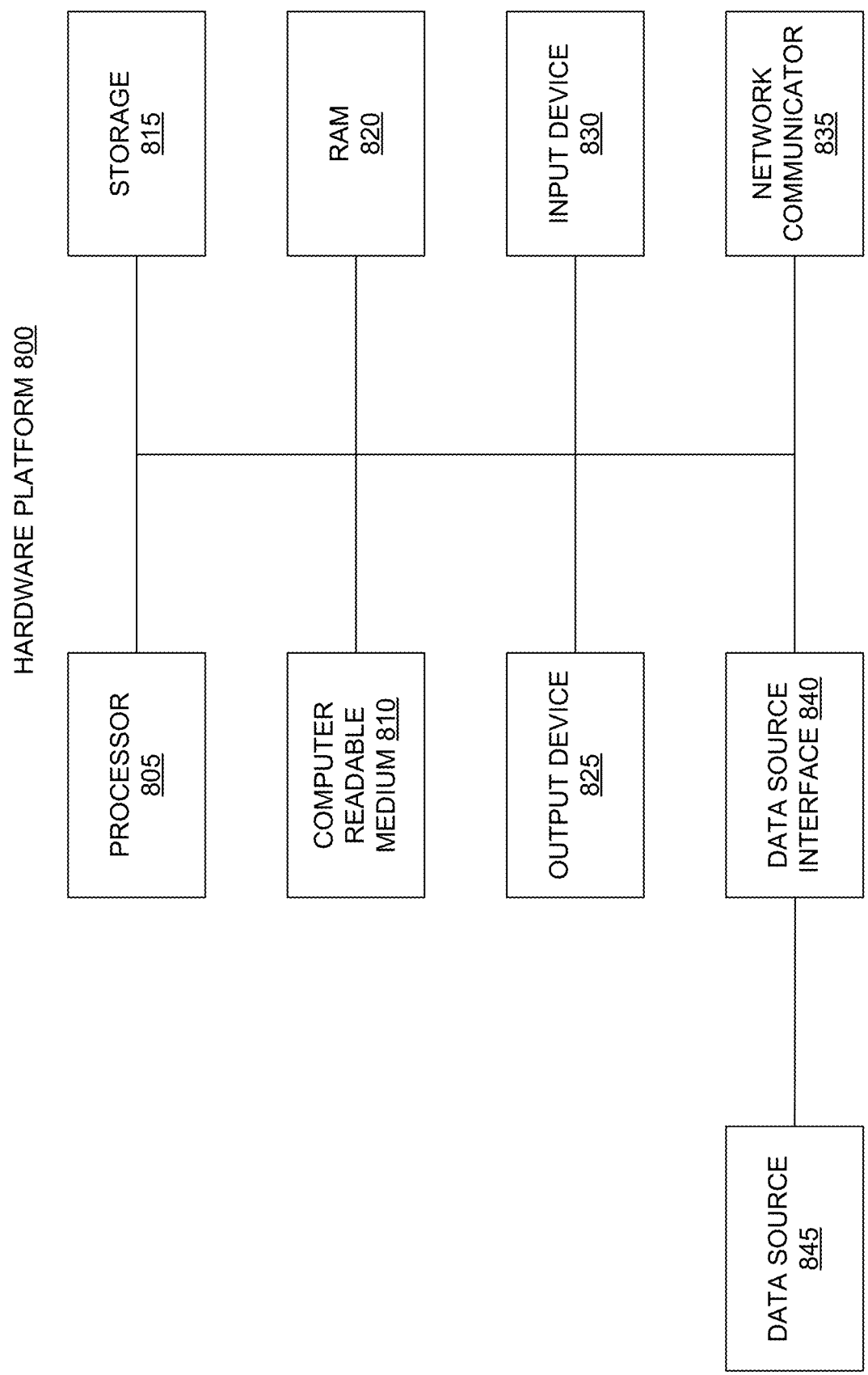
FIG. 8 illustrates a hardware platform for embodiment of the system, according to an example embodiment of the present disclosure.

FIG. 8 illustrates a hardware platform 800 for embodiment of the system 100, according to an example embodiment of the present disclosure. Particularly, computing machines such as but not limited to internal/external server clusters, quantum computers, desktops, laptops, smartphones, tablets and wearables which may be used to execute the system 100 or may have the structure of the hardware platform 800. The hardware platform 800 may include additional components not shown and that some of the components described may be removed and/or modified. In another example, a computer system with multiple GPUs can sit on external-cloud platforms including Amazon Web Services, or internal corporate cloud computing clusters, or organizational computing resources, etc.

Over the FIG. 8, the hardware platform 800 may be a computer system 800 that may be used with the examples described herein. The computer system 800 may represent a computational platform that includes components that may be in a server or another computer system. The computer system 800 may execute, by a processor (e.g., a single or multiple processors) or other hardware processing circuit, the methods, functions and other processes described herein. These methods, functions and other processes may be embodied as machine readable instructions stored on a computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory). The computer system 800 may include a processor 805 that executes software instructions or code stored on a non-transitory computer readable storage medium 810 to perform methods of the present disclosure. The software code includes, for example, instructions to detect an issue and forward the issue for processing, collect data from other employees and teams, analyze the data to determine a solution for the issue and provide the solution to the employee.

The instructions on the computer readable storage medium 810 are read and stored the instructions in storage 815 or in random access memory (RAM) 820. The storage 815 provides a large space for keeping static data where at least some instructions could be stored for later execution. The stored instructions may be further compiled to generate other representations of the instructions and dynamically stored in the RAM 820. The processor 805 reads instructions from the RAM 820 and performs actions as instructed.

The computer system 800 further includes an output device 825 to provide at least some of the results of the execution as output including, but not limited to, visual information to the employees about the solution and response to their query. The output device 825 can include a display on computing devices and virtual reality glasses. For example, the display can be a mobile phone screen or a laptop screen. GUIs and/or text are presented as an output on the display screen. The computer system 800 further includes input device 830 to provide a user or another device with mechanisms for entering data and/or otherwise interact with the computer system 800. The input device may include, for example, a keyboard, a keypad, a mouse, or a touchscreen. In an example, output of a bot is displayed on the output device 825. Each of these output devices 825 and input devices 830 could be joined by one or more additional peripherals.

A network communicator 835 may be provided to connect the computer system 800 to a network and in turn to other devices connected to the network including other clients, servers, data stores, and interfaces, for instance. The network communicator 835 may include, for example, a network adapter such as a LAN adapter or a wireless adapter. The computer system 800 includes a data source interface 840 to access data source 845. A data source is an information resource. As an example, a database of exceptions and rules may be a data source. Moreover, knowledge repositories and curated data may be other examples of data sources.

Figure 9:
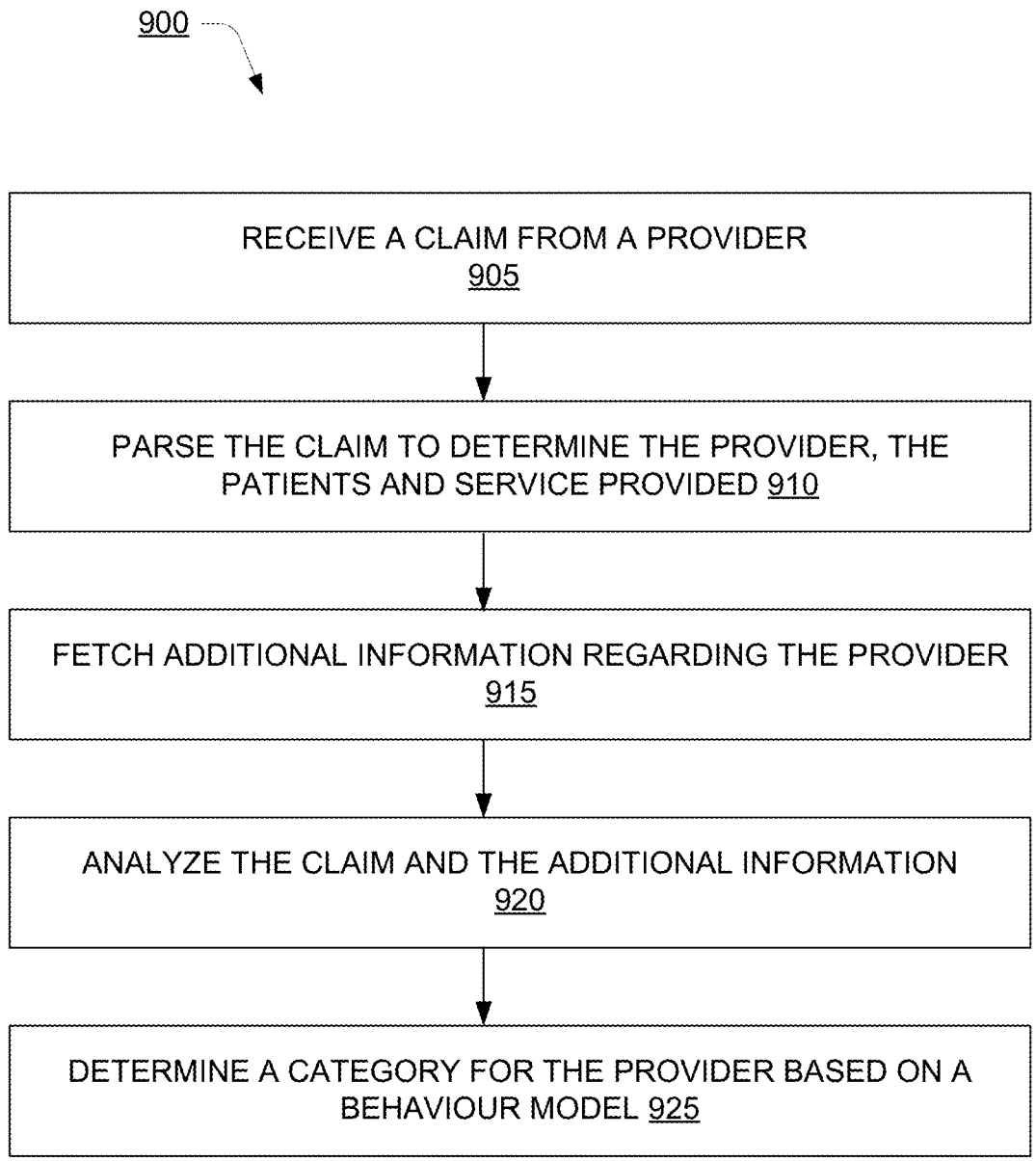
FIG. 9 illustrates a method for determining category for the provider, according to an example embodiment of the present disclosure.
Figure 10:
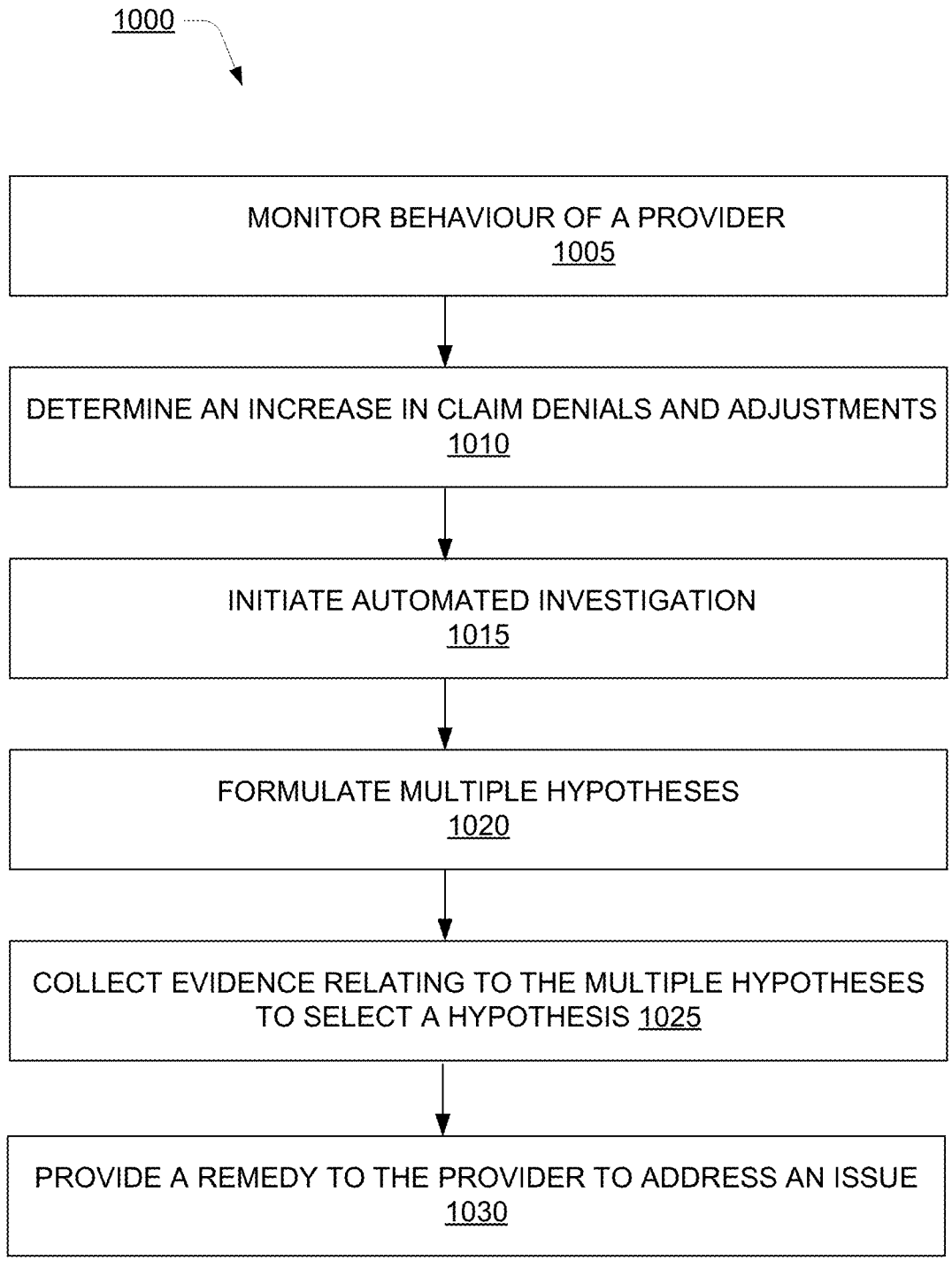
FIG. 10 illustrates a method for providing a remedy to address an issue in behaviour of a provider, according to an example embodiment of the present disclosure.
Figure 11:
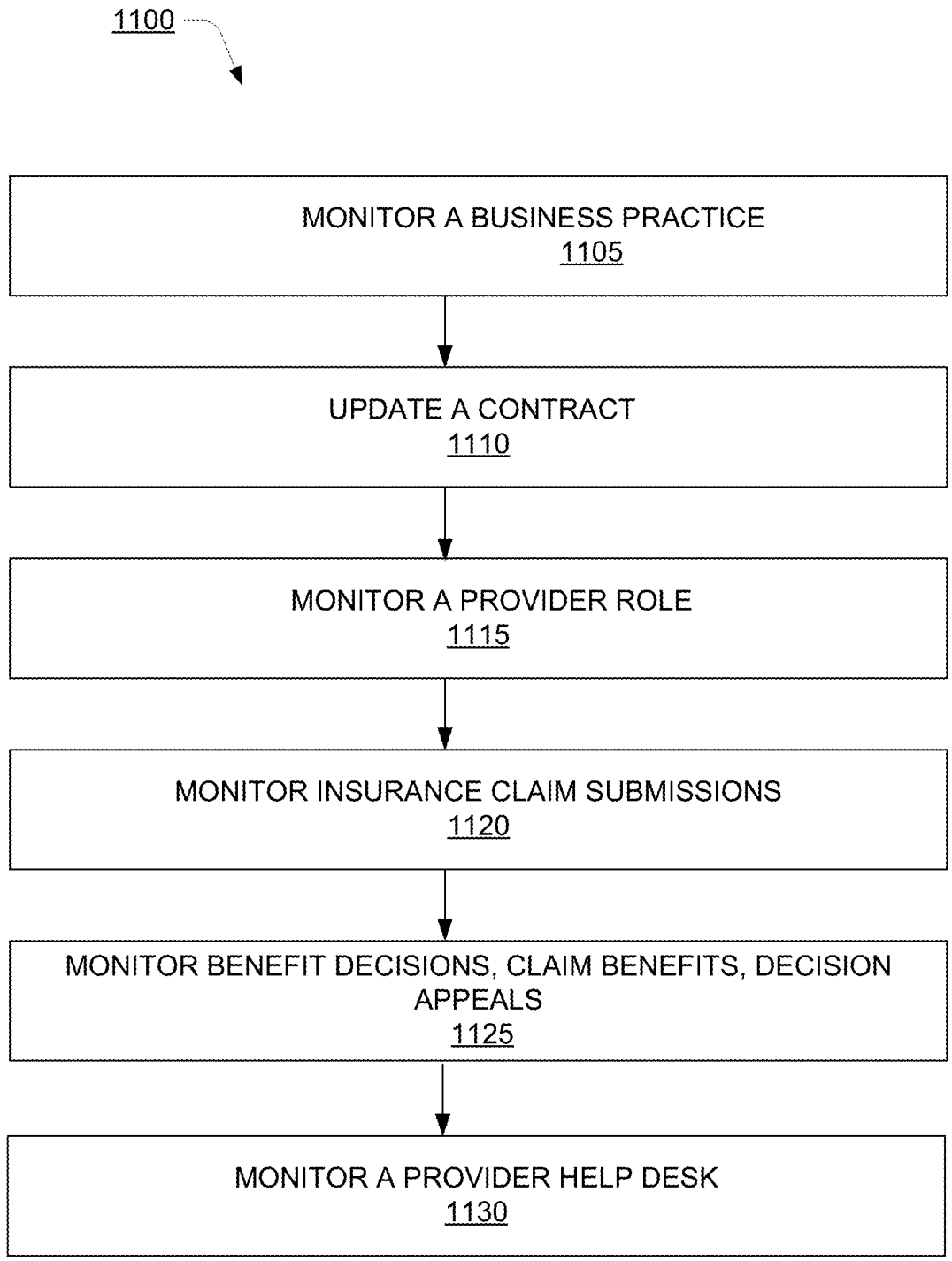
FIG. 11 illustrates a method for monitoring various parameters for detecting behaviour of a provider, according to an example embodiment of the present disclosure.
Figure 12:
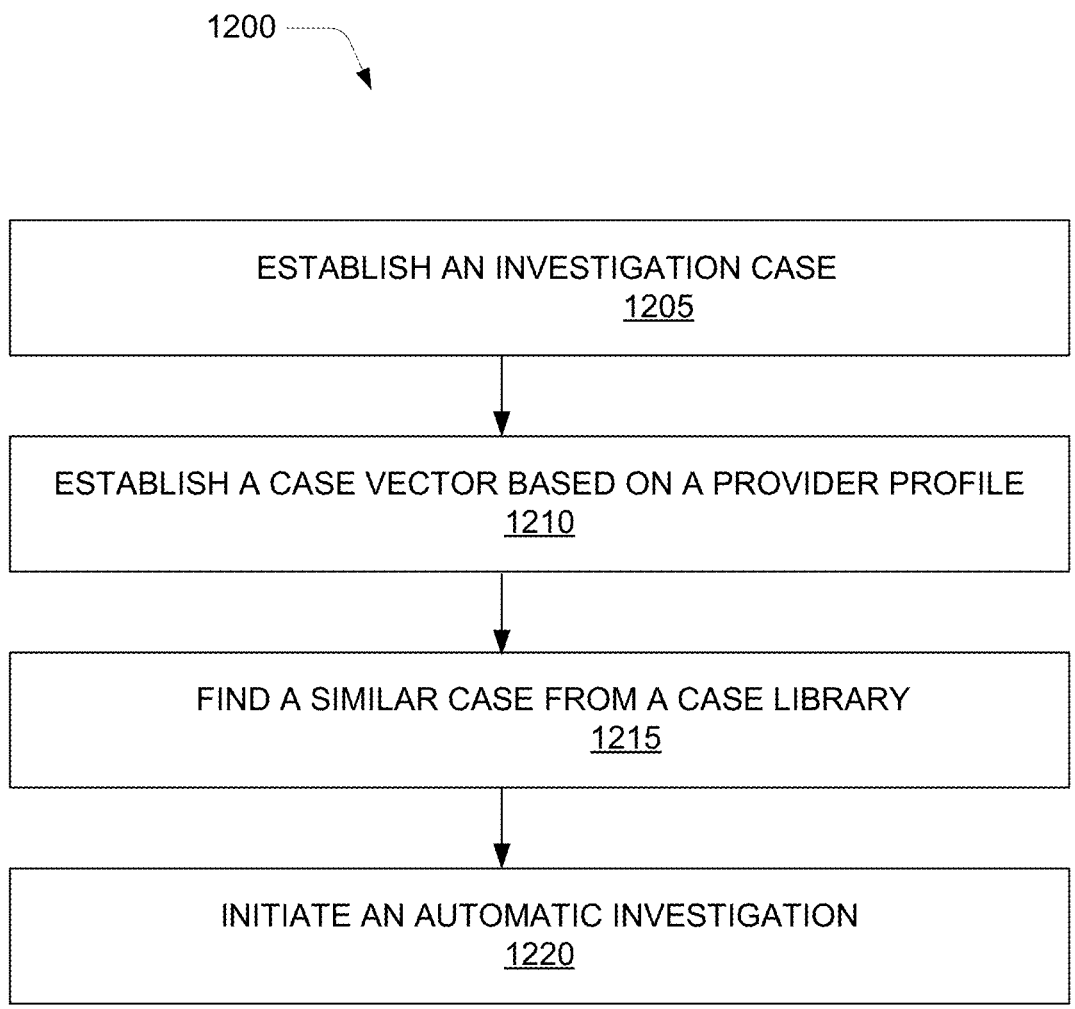
FIG. 12 illustrates a method for initiating an automated investigation for a provider, according to an example embodiment of the present disclosure.
Figure 13:
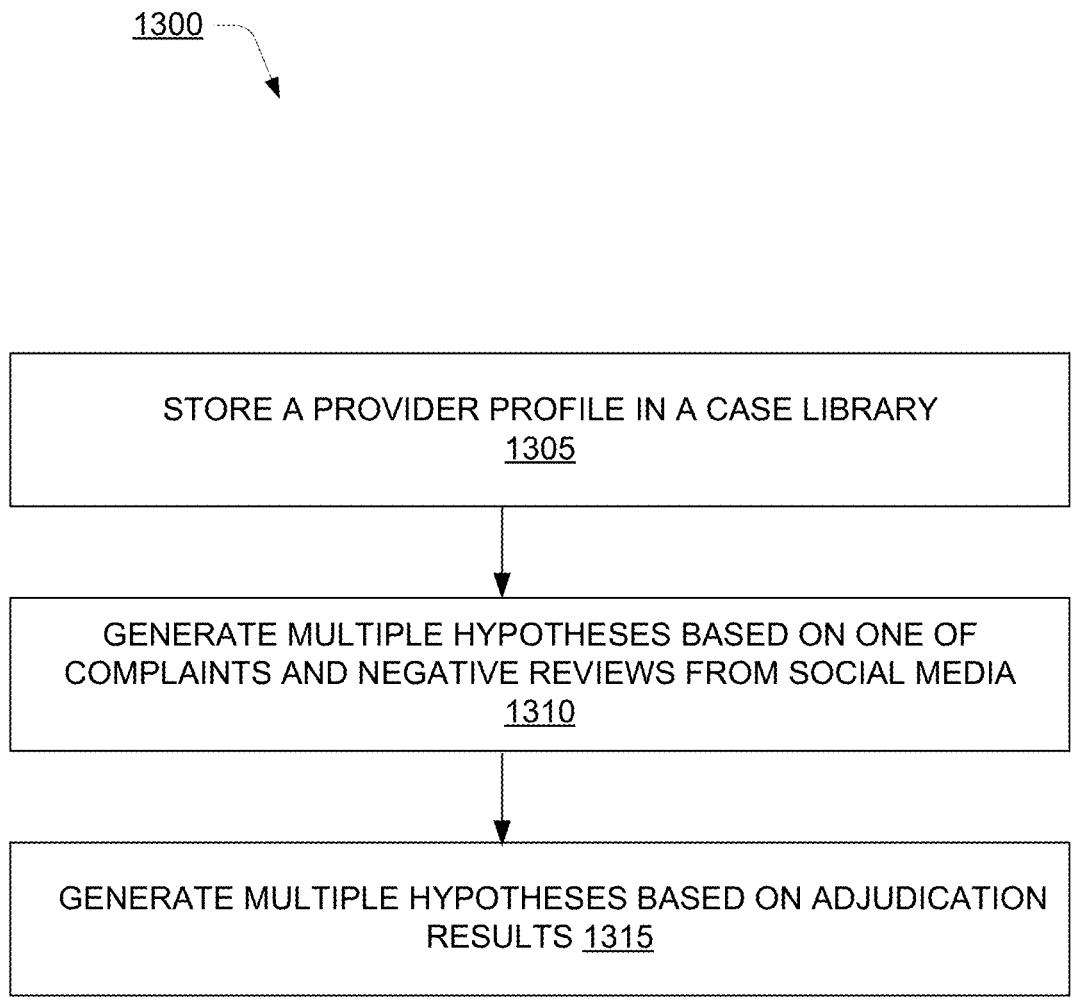
FIG. 13 illustrates a method for generating multiple hypotheses for an issue in behaviour of a provider, according to an example embodiment of the present disclosure.
Figure 14:
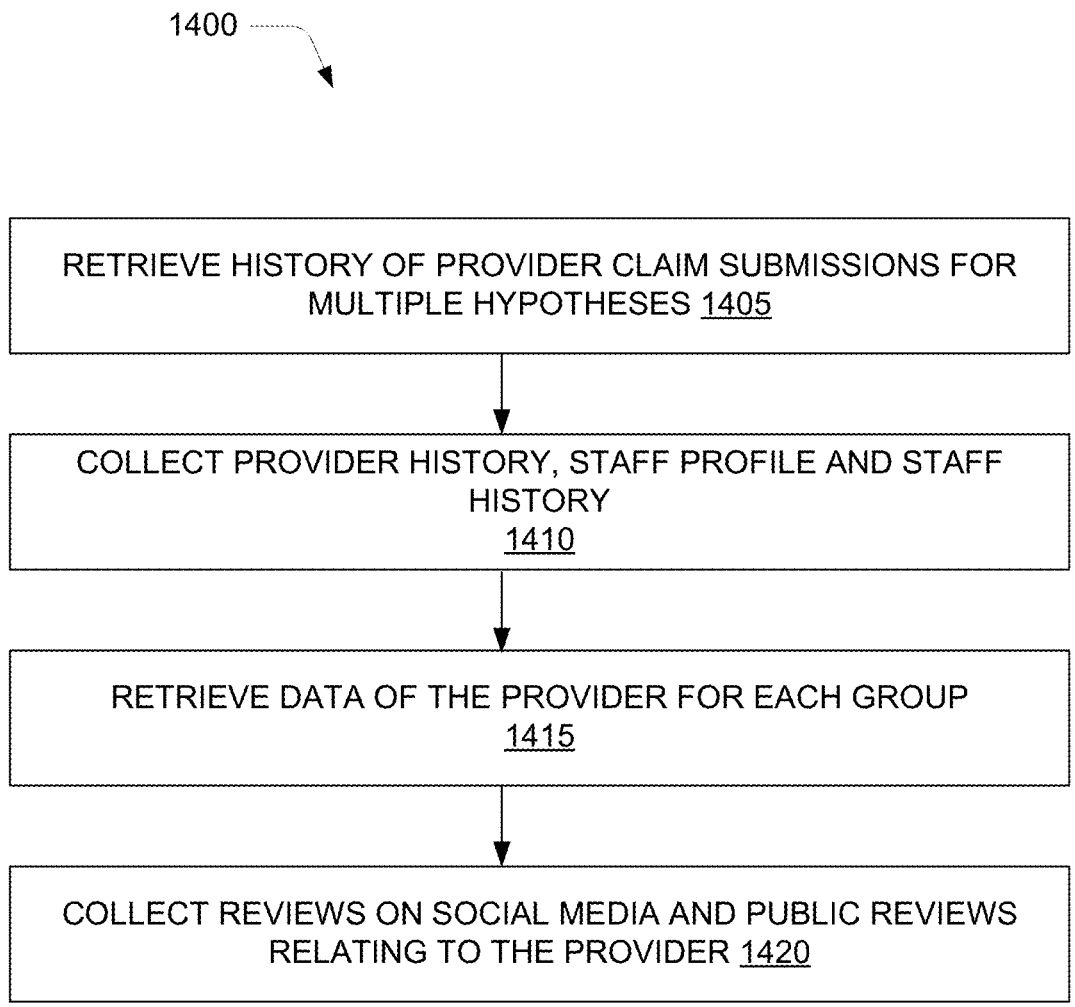
FIG. 14 illustrates a method for collecting reviews on social media and public reviews related to a provider, according to an example embodiment of the present disclosure.
Figure 15:
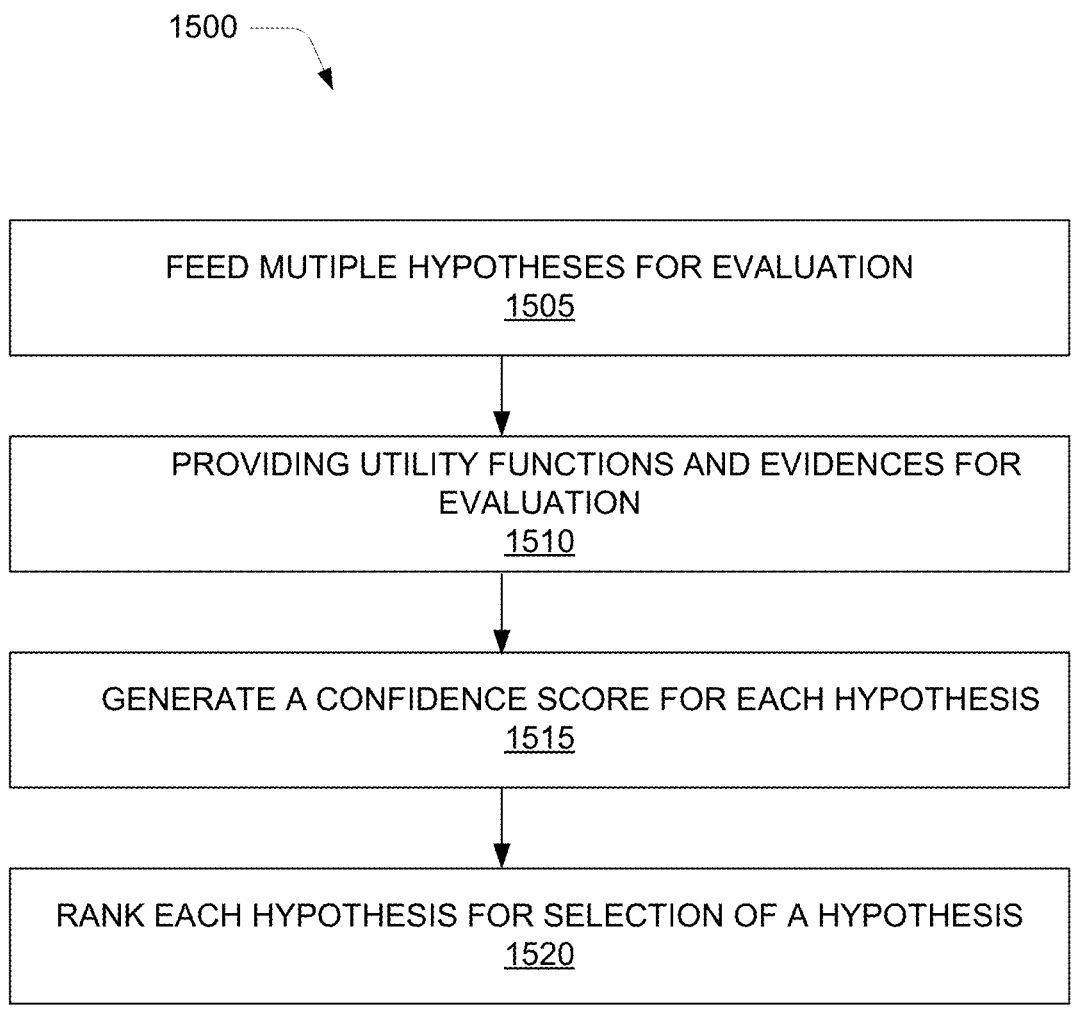
FIG. 15 illustrates a method for selecting a hypothesis, according to an example embodiment of the present disclosure.
Figure 16:
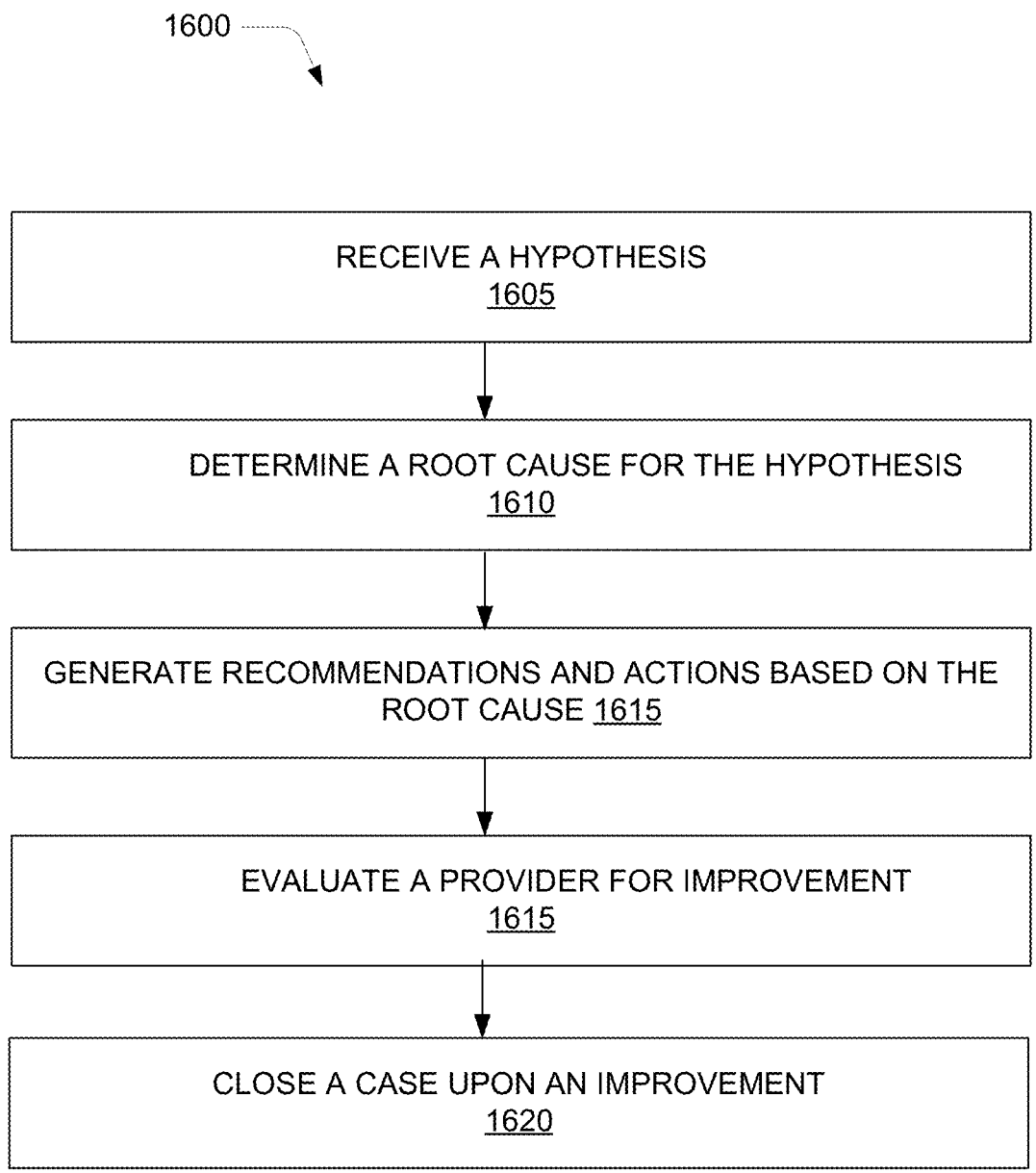
FIG. 16 illustrates a method for evaluating a provider for improvement and closing a case, according to an example embodiment of the present disclosure.

FIG. 9 shows a method 900 for determining a category for the provider, FIG. 10 shows a method 1000 for providing a remedy to address an issue in behaviour of a provider, and FIG. 11 illustrates a method 1100 for monitoring various parameters for detecting behaviour of a provider, according to an example embodiment of the present disclosure. Further, FIG. 12 shows a method 1200 for initiating an automated investigation for a provider, FIG. 13 illustrates a method 1300 for generating multiple hypotheses for an issue in behaviour of a provider, FIG. 14 shows a method 1400 for collecting reviews on social media and public reviews related to a provider, FIG. 15 shows a method 1500 for selecting a hypothesis from multiple hypotheses, and FIG. 16 illustrates a method for evaluating a provider for improvement and closing a case, according to an example embodiment of the present disclosure.

It should be understood that method steps are shown here for reference only and other combination of the steps may be possible. Further, the methods 900, 1000, 1100, 1200, 1300, 1400, 1500, and 1600 may contain some steps in addition to the steps shown in the FIG. 9, FIG. 10, FIG. 11, FIG. 12, FIG. 13, FIG. 14, FIG. 15, and FIG. 16, respectively. For the sake of brevity, construction and operational features of the system 100 which are explained in detail in the description of FIG. 1, FIG. 2, FIG. 3, FIG. 4 and FIG. 5 are not explained in detail in the description of FIG. 9, FIG. 10, FIG. 11, FIG. 12, FIG. 13, FIG. 14, FIG. 15, and FIG. 16. The methods 900, 1000, 1100, 1200, 1300, 1400, 1500, and 1600 may be performed by components of the system 100.

At block 905, an claim may be received. The claim may be filed by a provider who provides health and medical services to multiple patients. In an example, the claim analyzer 105 may receive the claim. At block 910, the claim may be parsed to determine the provider, the multiple patients and the details of the services provided to the multiple patients. Thereafter, at block 915, additional information related to the provider may be fetched. The additional information may include number of claims filed in the past, status of each claim, number of appeals filed in the past and status of the each appeal filed. In an example, the claim analyzer 105 may parse the claim to determine the provider, the multiple patients and the service provided, and fetches the additional information about the provider.

The claim and the additional information related to the provider may be analyzed, at block 920. Based on the analysis, a category may be selected for the provider, at block 925. In an example, the behaviour classifier 110 may analyze the claim and the additional information to determine the category for the provider.

Referring to method 1000, at block 1005, behaviour of the provider may be monitored. In one example, the behaviour monitor 115 may monitor the behaviour of the provider. The behaviour monitor 115 may perform the monitoring in an ongoing manner such that any change in behaviour may be tracked and recorded. At block 1010, increase in claim denials and adjustments may be determined. For example, if there has been a rise in the claim denials for the claims filed by the provider in the last six to seven months. At block 1015, an automated investigation may be initiated. The investigation is performed to determine an issue for the change in behaviour and provide a remedial action. The investigator 120 may initiate the automated investigation.

At block 1020, multiple hypotheses may be formulated related to the change in behaviour. In one example, the investigator 120 may formulate the multiple hypotheses. Thereafter, at block 1025, evidence may be collected relating to multiple hypotheses and based on the evidence a hypothesis may be selected. In one example, the investigator 120 may collect the evidence regarding the multiple hypotheses to select the hypothesis. At block 1030, a remedy may be provided to the provider to address the issue. In one example, the remediator 125 may determine the remedy and provide the remedy to the provider.

FIG. 11 shows the method 1100 for monitoring various parameters related to the provider, according to an example embodiment of the present disclosure. At block 1105, a business practice of the provider may be monitored. The business practice may be a solo practice where the provider operates independently as the service provider and a group practice where the provider operates as a member of a group to provide services to multiple patients. In one example, the behaviour monitor 115 may monitor the business practice of the provider.

At block 1110, a contract may be updated. The contract includes various definitions and policies for the provider to work with the payer. In a case, where business practice of the provider changes then various definitions and policies may also have to be updated in the contract. In one example, the contract updater 140 may update the contract based on the change in behaviour of the provider. At block 1115, the provider role may be monitored. The provider role may be the actual service provided by the provider. This may include, for example. internal medicine, orthopaedic, dentistry, or some of the specialist areas. Thereafter, at block 1120, claim submissions by the provider may be monitored. The claim submissions may include monitoring number of claims submitted by the provider in the past, the status of each claim whether accepted, rejected, denied or adjusted. In one example, the behaviour monitor 115 may monitor the claim submissions for the provider.

At block 1125, benefit decisions, claim benefits and decisions appeals may be monitored. In an example, an interaction with a call centre or a help desk may also be monitored including recorded calls and chats with representatives of the call centre. The behaviour monitor 115 may monitor the benefit decisions, claim benefits and the decision appeals. Thereafter, at block 1130, calls made by the provider to the helpdesk or any other correspondence between the provider and the helpdesk may also be monitored. The behaviour monitor 115 may monitor the calls and recorded correspondence between the provider and the helpdesk.

Referring to method 1200, at block 1205, an investigation case may be established. In one example, the investigation case may be established by the investigator 120. Thereafter, a case vector may be established at block 1210. In an example, the claim vector may be established based on parameters on a claim form, for instance, a form from Centre of Medicare and Medicaid, CMS-1500. This form may include the details of the providers, demographics of the patients, diagnosis codes and procedure codes corresponding to a procedure involved in diagnosing and treating. The investigator 120 may establish the case vector for the investigation case. After establishing the case vector, a similar case may be determined from a case library at 1215. In an example, the case vector may be indicative of a case and the similarity of the cases may be determined based on a distance metric, such as an Euclidian distance. The case vector may include key attributes of the case, such as the type of the provider, nature of the claim, and origin of a dispute. The similar case provides data related to type of behaviours and issues were detected in the past, the type of hypotheses determined for the provider and the remedy suggested. The investigator 120 may find the similar case from the case library. Thereafter, at block 1220, an automatic investigation may be initiated to derive multiple hypotheses. In one example, the investigator 120 may initiate the automated investigation.

The method 1300 is for generating multiple hypotheses based on adjudication results according to an embodiment of the present disclosure. At block 1305, a provider profile may be stored in the case library. The case library stores the profiles of multiple providers and serves as a database for fetching information related to providers for investigation purpose. For instance, in a case where the behaviour of the provider is similar to the behaviour profile of another provider, then the profile of the other provider may be referred to for deducing hypotheses. In an example, the behaviour classifier 110 may stores the provider profile in the case library. At block 1310, multiple hypotheses may be generated based on complaints of the provider on public databases and negative reviews from the social media. In an example, the hypotheses may be generated based on a potential issue, for instance, incorrect coding of a claim, an inquiry about the claim, or an appeal on the decision of the claim. The hypothesis for incorrect coding of the claim may be due to insufficient training of the staff, or malicious intent to commit a fraud, or to maximize benefit calculation. The hypothesis for the inquiry may be about a status of the claim or clarification of the filing procedure for the claim. The appeal of the decision may be related to a decision on eligibility for benefit payment or the benefit calculation. The investigator 120 may generate the multiple hypotheses from the complaints raised against the provider and the negative reviews and feedback related to the provider.

Thereafter, at block 1315, multiple hypotheses may be generated based on adjudication results for the claim. The adjudication results may be whether claims from a provider are denied, approved or adjusted. For instance, if the claims from a provider have been approved, then a hypothesis of the provider making fewer errors in filing the claim due to more awareness may be deduced. In an example, the investigator 120 may generate the multiple hypotheses based on the adjudication results.

Referring to method 1400, at block 1405, for multiple hypotheses history of claim submissions may be retrieved. The history may include information, such as number of claims filed by a provider, status of each claim whether approved or denied, reasons given for denial of the claims, actions taken by the provider after denial of the claims. The investigator 120 may retrieve the history of the claim submissions. At block 1410, history of the provider, profile of staff and history of the staff may be retrieved. The history of the provider may include number of patients treated by the provider, feedback and ratings of the multiple patients, experience of the patients with the provider, the provider's previous business practice and performance of the provider. Further, the provider may also have staff for handling and managing the patients. The profile of the staff may include qualifications, expertise and skills of members of the staff to determine whether they are qualified to handle the patients and help the provider in providing the service to the patients. The history of the staff may include performance of the members of the staff in the current facility and previous facilities, ratings and feedbacks of providers, facility owners and patients regarding the members of the staff. Thereafter, at block 1415, data related to the provider for each group may be retrieved. In an example, the investigator 120 may retrieve the data for a provider for each group. After retrieving the data, reviews on social media and public reviews relating to the provider may be collected. In an example, the investigator 120 may collect reviews on social media and public reviews relating to the provider.

FIG. 15 illustrates the method 1500 for selecting a hypothesis based on rank, according to an example embodiment of the present disclosure. At block 1505, multiple hypotheses may be fed for evaluation. Thereafter, utility functions and evidences are provided for the evaluation, at block 1510. The utility functions may be utilized to determine likelihood of the multiple hypotheses and aid in selecting the most likely hypothesis. For example, based on coding for a claim, the utility function may evaluate at least one of whether a provider has taken a cautious approach to determine the medical necessity, whether a diagnosis is plausible, whether a procedure is consistent with the diagnosis, or is more intense, and whether a coder has considered interdependencies among different procedures. In an example, the investigator 120 may feed the multiple hypotheses for evaluation and then provide the utility functions and the evidences for evaluation. At block 1515, confidence scores may be generated for each hypothesis. The confidence scores may be generated by the investigator 120. Thereafter at block 1520, each hypothesis may be ranked and a hypothesis may be selected based on the rank. In an example, the investigator 120 may rank each hypothesis and then select the hypothesis based on the rank.

Method 1600 relates to evaluating a provider for improvement for closing a case. At block 1605, a hypothesis may be received. In an example, the hypothesis may be received by the claim analyzer 105. At block 1610, a root cause for the hypothesis may be determined. The claim analyzer 105 may determine the root cause for the hypothesis. At block 1615, recommendations and actions may be generated based on the root cause. In one example, the recommendations include one of an additional training for staff of the provider, eliminating bias for claim submission, adjusting benefit request in the claim, improving facility of the provider, an additional training for the provider. After generating the recommendations, the provider may be monitored for improvement. At block 1615, the provider may be evaluated for an improvement in behaviour for filing the claims. The improvement may be detected based on, for instance, reduction in claim denials and rise in number of claim approvals. Upon detecting the improvement in the behaviour of the provider, the case may then be closed at block 1620.

What has been described and illustrated herein are examples of the present disclosure. The terms, descriptions and figures used herein are set forth by way of illustration only and are not meant as limitations. Many variations are possible within the spirit and scope of the subject matter, which is intended to be defined by the following claims and their equivalents in which all terms are meant in their broadest reasonable sense unless otherwise indicated.

We claim:

1. A medical concierge system (MCS) comprising:
a processor to:
receive a claim from a provider, the claim comprising data relating to a service provided, by the provider, to multiple patients, the data relating to the service provided being indicative of a number of visits, treatment plans, and medical expense for each of the multiple patients;
parse the claim to determine the provider, the multiple patients and the data relating to the service provided;
fetch additional information regarding the provider, the additional information comprising at least one of a number of claims filed in the past, a status of each claim for approval, a number of appeals filed by the provider, a status of the appeals as approved and denied, and complaints registered by the provider;
analyze the claim and the additional information for at least one of a number of claims denied, a number of claims rejected, a number of claims approved, a number of appeals filed, a number of appeals approved, and a number of appeals denied based on a predefined threshold;
determine a category for the provider based on a comparison of the analyzed claims and the additional information with predefined thresholds;
monitor at least one of a number of claims filed by the provider, a number of visiting patients to the provider, reviews of the provider, ratings of the provider, a feedback of the provider on social media, and complaints against the provider;
determine an increase in one of claim denials associated with the provider and claim adjustments associated with the provider;
determine a change in the category of the provider based on the monitoring and the determining of the increase in of the claim denials and the claim adjustments;
update the category of the provider based on the determining of the change in the category of the provider;
analyze the claim, the additional information, and the category for the provider to determine an issue;
deduce multiple hypothesis and select a hypothesis among the multiple hypothesis to resolve the issue based on at least one of an incorrect coding of the claim, an inquiry about the claim, or an appeal filed on a decision of the claim, and the determined issue, wherein deducing multiple hypothesis comprises:
establishing a case vector based on parameters of the claim, wherein the parameters include details of demographics of the multiple patients and diagnosis codes and procedure codes corresponding to a procedure involved diagnosis; and
identifying another case based on the case vector from a case library, wherein the another case provides data related to issues that were detected in the past, hypotheses determined for the provider in the past, and the remedy suggested in the past, wherein the another case is identified based on an Euclidian distance.

2. The MCS as claimed in claim 1, wherein the processor is further to:
collect an evidence relating to one of medical conditions of patients associated with the claim, medical history of the patients associated with the claims, and effect of treatment on the patients associated with the claim;
select the hypothesis from among the multiple hypothesis based on the evidence;
analyze the hypothesis based on one of coding mistakes in filing claims, an aggressive claim filing, and an inconsistency between a diagnosis and a procedure performed to determine a remedy to resolve the issue;
generate an alert for the issue; and
provide the alert for the issue and the remedy to the provider for resolving the issue.

3. The MCS as claimed in claim 1, wherein the processor is further to:

determine a change in a provider profile based on one of
information shared by the provider;
fetch information relating to the changed profile of the
provider; and
update the provider profile with the fetched information in
a database.

4. The MCS as claimed in claim 3, wherein the processor is further to:
determining whether the updated provider profile is covered under an existing contract; and
when the updated profile is not covered under the existing contract
update the existing contract based on the updated profile and a stored set of contracts.

5. A method comprising:
receiving a claim from a provider, the claim comprising data relating to a service provided, by the provider, to multiple patients, the data relating to the service provided being indicative of a number of visits, treatments plans, and medical expense for each of the multiple patients;
parsing the claim to determine the provider, the multiple patients and the data relating to the service provided; and
fetching additional information regarding the provider, the additional information comprising at least one of a number of claims filed in the past, a status of each claim for approval, a number of appeals filed by the provider, a status of the appeals as approved and denied, and complaints registered by the provider;
analyzing the claim and the additional information for at least one of a number of claims denied, a number of claims rejected, a number of claims approved, a number of appeals filed, a number of appeals approved, and a number of appeals denied based on a predefined threshold;
determining a category for the provider based on a comparison of the analyzed claims and the additional information with predefined thresholds;
monitoring at least one of a number of claims filed by the provider, a number of visiting patients to the provider, reviews of the provider, ratings of the provider, a feedback of the provider on social media and complaints against the provider;
determining an increase in one of claim denials associated with the provider and claim adjustments associated with the provider;
determining a change in the category of the provider based on the monitoring and the determining of the increase in of the claim denials and the claim adjustments;
updating the category of the provider based on the determining of the change in the category of the provider;
analyzing the claim, the additional information, and the category for the provider to determine an issue;
deducing multiple hypothesis and select a hypothesis among the multiple hypothesis to resolve the issue based on at least one of an incorrect coding of the claim, an inquiry about the claim, or an appeal filed on a decision of the claim, and the determined issue, wherein deducing multiple hypothesis comprises:
establishing a case vector based on parameters of the claim, wherein the parameters include details of demographics of the multiple patients and diagnosis codes and procedure codes corresponding to a procedure involved diagnosis; and
identifying another case based on the case vector from a case library, wherein the another case provides data related to issues that were detected in the past, hypotheses determined for the provider in the past, and the remedy suggested in the past, wherein the another case is identified based on an Euclidian distance.

6. The method as claimed in claim 5 further comprising:
collecting an evidence relating to one of medical conditions of patients associated with the claim, medical history of the patients associated with the claims, and effect of treatment on the patients associated with the claim;
selecting the hypothesis from amongst the multiple hypotheses based on the evidence; and
providing a remedy to the provider to address the issue.

7. The method as claimed in claim 6, wherein formulating the multiple hypotheses comprises:
storing a provider profile in a case library, the provider profile including data relating to a business profile, a number of patients, treatments plans, an experience and training of the provider; and
analyzing complaints, negative reviews on social media, and adjudication result for the claim.

8. The method as claimed in claim 6, wherein selecting the hypothesis comprises:
ranking each hypothesis of the multiple hypothesis based on a confidence score corresponding to each hypothesis; and
selecting the hypothesis based on the rank.

9. The method as claimed in claim 6, wherein collecting the evidence comprises:
retrieving history of claim submissions by the provider from a claim database;
collecting a provider profile, a staff profile and a history of staff;
retrieving data relating to the provider for a group;
collecting ratings and public reviews related to the provider from social media; and
analyze the hypothesis based on the collected ratings and reviews to resolve the issue.

10. The method as claimed in claim 6, wherein providing the remedy comprises:
receiving the hypothesis;
generating a recommendation that includes at least one of an additional training for staff of the provider, eliminating bias for claim submission, adjusting benefit request in the claim, improving facility of the provider, an additional training for the provider;
evaluating the provider for improvement in the claim submission; and
closing the case upon determining the improvement.

11. A non-transitory computer readable medium including machine readable instructions that are executable by a processor to:
receive a claim from a provider, the claim comprising data relating to a service provided, by the provider, to multiple patients, the data relating to the service provided being indicative of a number of visits by the multiple patients, treatment plans, and medical expense for each of the multiple patients;
parse the claim to determine the provider, the multiple patients and the data relating to the service provided;
fetch additional information regarding the provider, the additional information comprising at least one of a number of claims filed in the past, a status of each claim for approval, a number of appeals filed by the provider, a status of the appeals as approved and denied, and complaints registered by the provider;

analyze the claim and the additional information for at least one of a number of claims denied, a number of claims rejected, a number of claims approved, a number of appeals filed, a number of appeals approved, and a number of appeals denied based on a predefined threshold; and determine a category for the provider based on a comparison of the analyzed claims and the additional information with predefined thresholds;

monitor at least one of a number of claims filed by the provider, a number of visiting patients to the provider, reviews of the provider, ratings of the provider, a feedback of the provider on social media, and complaints against the provider;

determine an increase in one of claim denials associated with the provider and claim adjustments associated with the provider;

determine a change in the category of the provider based on the monitoring and the determining of the increase in of the claim denials and the claim adjustments;

update the category of the provider based on the determining of the change in the category of the provider;

analyze the claim, the additional information, and the category for the provider to determine an issue;

deduce multiple hypothesis and select a hypothesis among the multiple hypothesis to resolve the issue based on at least one of an incorrect coding of the claim, an inquiry about the claim, or an appeal filed on a decision of the claim, and the determined issue, wherein deducing multiple hypothesis comprises:

establishing a case vector based on parameters of the claim, wherein the parameters include demographics of the multiple patients and diagnosis codes and procedure codes corresponding to a procedure involved diagnosis; and identifying another case based on the case vector from a case library, wherein the another case provides data related to issues that were detected in the past, hypotheses determined for the provider in the past, and the remedy suggested in the past, wherein the another case is identified based on an Euclidian distance.

12. The non-transitory computer readable medium as claimed in claim 11, wherein the processor is to:

collect an evidence relating to one of medical conditions of patients associated with the claim, medical history of the patients associated with the claims, and effect of treatment on the patients associated with the claim;

select the hypothesis from among the multiple hypothesis based on the evidence;

analyze the hypothesis based on one of coding mistakes in filing claims, an aggressive claim filing, and an inconsistency between a diagnosis and a procedure performed to determine a remedy to resolve the issue;

generate an alert for the issue; and provide the alert for the issue and the remedy to the provider for resolving the issue.

13. The non-transitory computer readable medium as claimed in claim 11, wherein the processor is further to:

determine a change in a provider profile based on one of an information shared by the provider and detecting a change in a practice of the provider, wherein the practice includes one of a solo practice and a group practice; and fetch information relating to the changed profile of the provider; and update the provider profile with the fetched information in a database.

14. The non-transitory computer readable medium as claimed in claim 13, wherein the processor is further to:

determine whether the updated provider profile is covered under an existing contract; and when the updated profile is not covered under the existing contract update the existing contract based on the updated profile and a stored set of contracts.

* * * * *

UNITED STATES PATENT AND TRADEMARK OFFICE
CERTIFICATE OF CORRECTION

PATENT NO. : 11,120,894 B2
APPLICATION NO. : 16/163252
DATED : September 14, 2021
INVENTOR(S) : Chung-Sheng Li et al.

It is certified that error appears in the above-identified patent and that said Letters Patent is hereby corrected as shown below:

In the Claims

In Column 17, Line 1, Claim 3, reads "on one of information" should read "on information".

Signed and Sealed this
Seventeenth Day of May, 2022

Katherine Kelly Vidal
*Director of the United States Patent and Trademark Office*